(12) United States Patent
Davis

(10) Patent No.: US 7,114,499 B2
(45) Date of Patent: Oct. 3, 2006

(54) RETRACTING EYE DRAPE

(76) Inventor: Andrew Peter Davis, 14360 SE. 47th Pl., Bellevue, WA (US) 98006

( * ) Notice: Subject to any disclaimer, the term of this patent is extended or adjusted under 35 U.S.C. 154(b) by 24 days.

(21) Appl. No.: 10/999,240

(22) Filed: Nov. 30, 2004

(65) Prior Publication Data

US 2005/0115569 A1 Jun. 2, 2005

Related U.S. Application Data

(60) Provisional application No. 60/526,443, filed on Dec. 2, 2003, provisional application No. 60/620,248, filed on Oct. 19, 2004.

(51) Int. Cl.
*A61B 19/00* (2006.01)
*A61B 19/08* (2006.01)
*A61F 5/37* (2006.01)

(52) U.S. Cl. .................. 128/850; 128/849; 128/853

(58) Field of Classification Search ............... 128/846, 128/849–855; 600/236, 201
See application file for complete search history.

(56) References Cited

U.S. PATENT DOCUMENTS

| | | | | |
|---|---|---|---|---|
| 4,412,532 A | * | 11/1983 | Anthony | .................. 600/206 |
| 5,361,780 A | * | 11/1994 | Kellan | .................. 128/849 |
| 6,070,587 A | * | 6/2000 | Levitt et al. | .................. 128/849 |
| 6,345,621 B1 | * | 2/2002 | Chandler et al. | .......... 128/849 |
| 6,345,622 B1 | * | 2/2002 | Chandler et al. | .......... 128/849 |
| 6,647,985 B1 | * | 11/2003 | Prywes | ................. 128/853 |
| 6,675,805 B1 | * | 1/2004 | Graether | ................. 128/849 |
| 6,863,071 B1 | * | 3/2005 | Annett et al. | .............. 128/849 |
| 2005/0159775 A1 | * | 7/2005 | Reynolds | ............... 606/205 |

* cited by examiner

*Primary Examiner*—Henry Bennett
*Assistant Examiner*—Kari Petrik
(74) *Attorney, Agent, or Firm*—Black Lowe & Graham PLLC

(57) ABSTRACT

A retracting eye drape assembly is disclosed for use around a patient's eye to seclude and seal off the operative field during eye surgery. The drape assembly includes a retraction member connected to the drape and configured to engage the patient's eyelid, an extension member connected to the retraction member or to the drape and configured to substantially enclose the patient's eyelid, and a retraction flap configured to secure the patient's eyelid in a substantially retracted position. A method of applying an eye drape assembly is disclosed. After application of the drape to the patient's face, and while the patient's eyelid is closed, the patient's eyelid is engaged by a retraction member connected to the drape and retracted. While retracted, the patient's eyelid is substantially enclosed to seclude the eyelid and eyelashes from the operational area. The secluded eyelid and eyelashes are then secured in a retracted position.

31 Claims, 18 Drawing Sheets

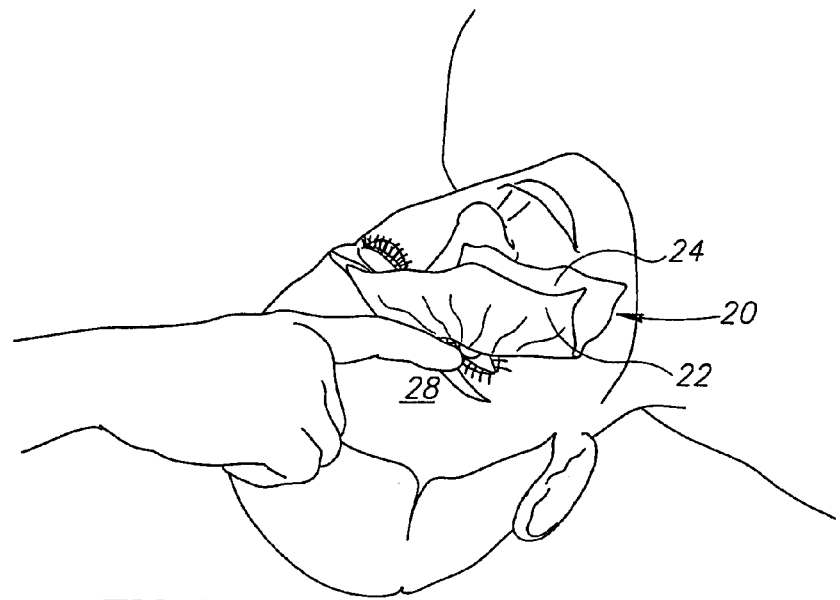
FIG.1
(PRIOR ART)
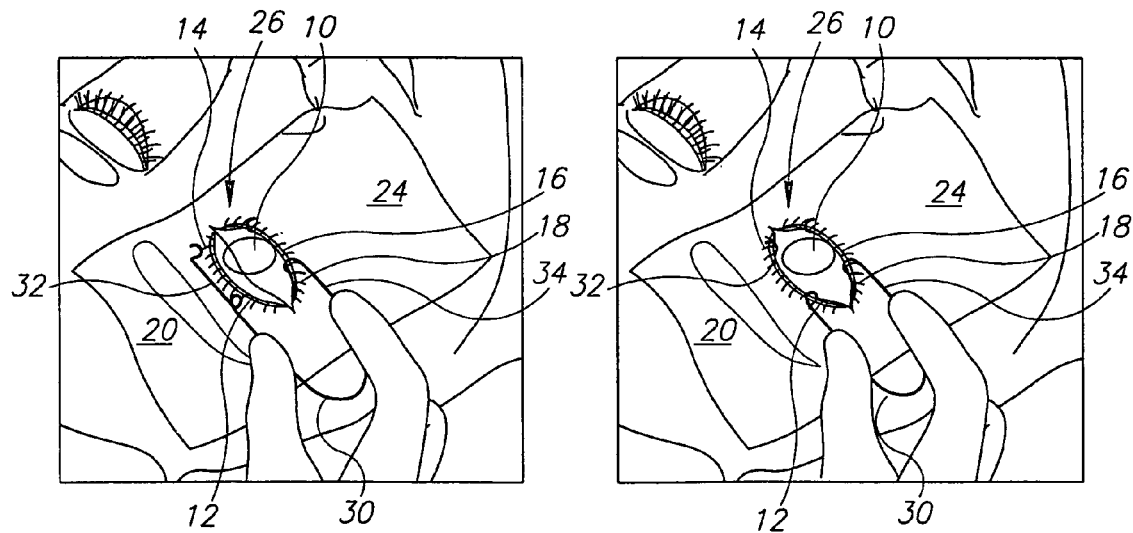
FIG.2
(PRIOR ART)
FIG.3
(PRIOR ART)

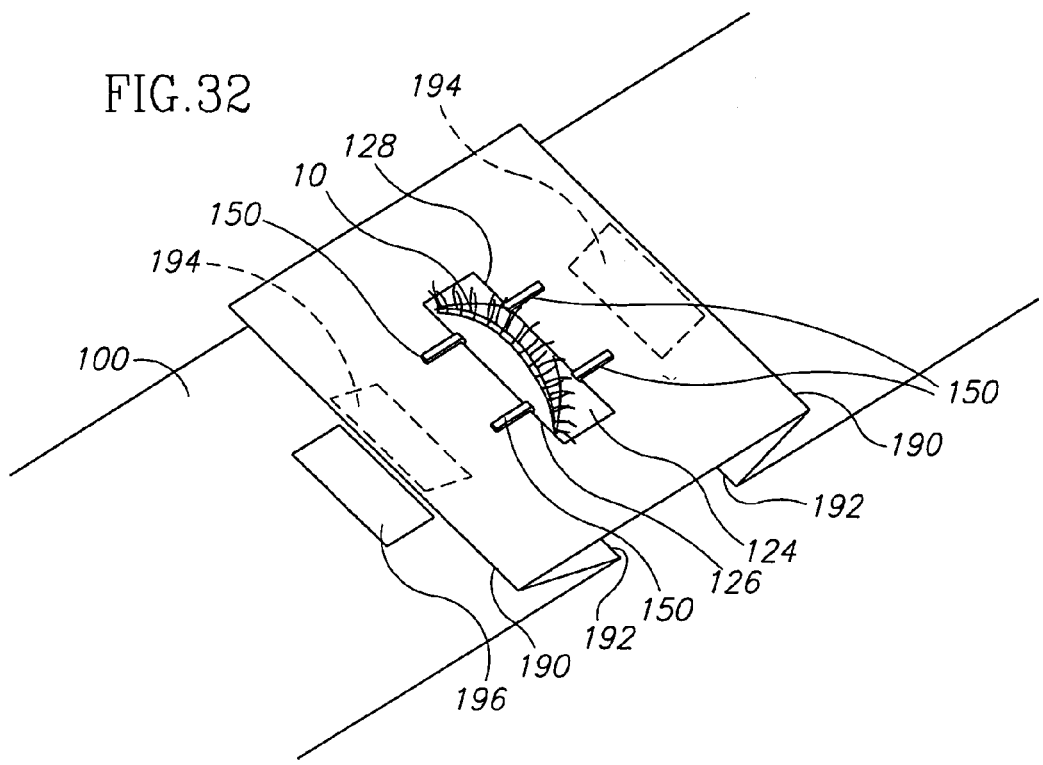

RETRACTING EYE DRAPE

PRIORITY CLAIM

This application claims priority to U.S. Provisional Application Nos. 60/526,443, filed Dec. 2, 2003, and 60/620,248, filed Oct. 19, 2004, which applications are hereby incorporated by reference in their entirety as if fully set forth herein.

FIELD OF THE INVENTION

This invention relates generally to surgical eye drapes and, more specifically, to a system and method for a retracting eye drape.

BACKGROUND OF THE INVENTION

As part of virtually every eye surgery, the facial area around the eye must be sealed off to expose the eye to the surgeon. Various techniques have been used to accomplish this goal. Most of the techniques incorporate the use of a sterilized surgical drape, typically made of plastic, having adhesive on one surface, together with an eyelid retraction device, typically a speculum.

The typical prior art technique for draping an eye 10 having an upper eyelid 12 with upper eyelashes 14 and a lower eyelid 16 having lower eyelashes 18 for surgery is described with reference to FIGS. 1–3. As shown in FIG. 1, the patient's upper eyelid 12 is held open, preferably with a sterile finger or tool (e.g., cotton tipped applicator stick) and the patient is asked to look down. A drape 20 having an adhesive surface 22 and a non-adhesive surface 24 is applied to the facial area 28 around the eye 10. After application of the drape with the eye open underneath the drape, a slit 26 is carefully cut extending at least the width of the eye. After the slit is cut in the drape, the drape 20 is positioned over the eye such that the slit 26 extends transversely over the eye and the drape extends to cover both the upper eyelid 12 (in its partially retracted position) and the lower eyelid 16.

As shown in FIGS. 2 and 3, once the drape is securely in place on the facial surface around the eye, a retractable eyelid speculum 30 having an upper arm 32 and a lower arm 34 is used to fully retract both eyelids. With reference to FIG. 2, a portion of the drape extending over the eye 10, lower eyelid 16 and lower eyelashes 18 is folded under the lower eyelid and lower eyelashes and held in place, in a retracted position, by the lower arm 34 of the speculum 30. With reference to FIG. 3, a portion of the drape extending over the eye 10, upper eyelid 12 and upper eyelashes 14 is folded under the upper eyelid and upper eyelashes and held in place, in a retracted position, by the upper arm 32 of the speculum 30. The drape 20 is maintained in place with relation to the eye by the adhesive surface 22 and the eye is fully exposed, in an open position, by virtue of the speculum 30 retracting both upper and lower eyelids and eyelashes.

As illustrated in the above description of the prior art technique, the available drapes require the eyelids to be held open while the drape is applied. This is awkward and cumbersome, and uncomfortable to the patient. Additionally, these techniques frequent result in a mild abrasive effect on the corneal surface during application of the drape. This in turn can make visualization of the eye difficult during surgery. In addition, as described above, the surgeon often has to cut an opening in the drape This is frightening to the patient, and increases the likely hood of cutting skin, or cutting an eyelash, or abrading the cornea. Frequently, the patient manages to squeeze their eyelids closed under the drape, eliminating the overlap of the drape to the lid margin, thus making it impossible for the drape to wrap around the lid margin.

Accordingly, there is a need for a system and method for a retracting eye drape that is easily applied without requiring the eyelids to be held open, that facilitates the incorporation of the eyelashes and lid margin and that reduces the possibility of corneal surface abrasion.

SUMMARY OF THE INVENTION

The present invention provides a retracting eye drape assembly for use around a patient's eye to seclude and seal off the operative field during eye surgery. The drape includes a non-adherent side and an adherent side, the adherent side amendable to adherence to the patient's facial area around the patient's eye. The drape assembly further includes a retraction member configured to engage the patient's eyelid, an extension member configured to substantially enclose the patient's eyelid, and a retraction flap configured to secure the patient's eyelid in a substantially retracted position.

The present invention further provides a method for applying a drape assembly for use around a patient's eye to seclude and seal off the operative field during eye surgery. The adherent side of a drape having a non-adherent side and an adherent side is applied to the patient's facial area around the patient's eye. While the patient's eyelid is closed, the patient's eyelid is engaged by a retraction member connected to the drape. The patient's eyelid is retracted using the retraction member. While retracted, the patient's eyelid is substantially enclosed to seclude the eyelid and eyelashes from the operational area. The secluded eyelid and eyelashes are then secured in a retracted position.

As will be readily appreciated from the foregoing summary, the invention provides system and method for a retracting eye drape that is easily applied without requiring the eyelids to be held open, that facilitates the incorporation of the eyelashes and lid margin that eliminates the need to cut the drape open and that reduces the possibility of corneal surface abrasion.

BRIEF DESCRIPTION OF THE DRAWINGS

Preferred and alternative embodiments of the present invention are described in detail below with reference to the following drawings.

FIG. 1 is an illustration of a prior art drape being applied around a patient's eye;

FIG. 2 is an illustration of a speculum used with a prior art drape to retract a patient's lower eyelid;

FIG. 3 is an illustration of a speculum used with a prior art drape to retract a patient's upper eyelid;

FIG. 32 is an illustration of a drape system in accordance with the invention that incorporates a single continuous drape folded into segments;

FIG. 33 is an illustration of the underside of the drape system shown in FIG. 32.

DETAILED DESCRIPTION OF THE PREFERRED EMBODIMENT

The present invention provides a new type of draping system, and method of applying the drape, prior to eye surgery. The drape is applied with the patient's eye closed, reducing the discomfort to the patient and risk of corneal surface abrasion. The drape and method of application also make it easier and less cumbersome for the surgeon to apply.

Figure 4:
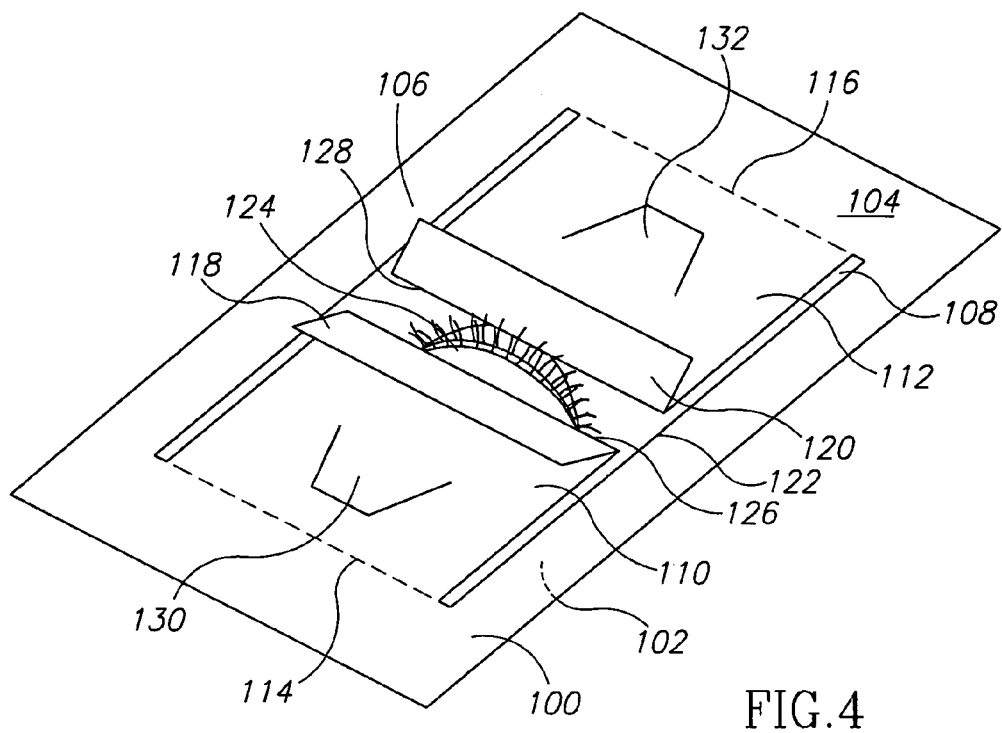
FIG. 4 is an illustration of a drape system in accordance with the invention.

With reference to FIG. 4, a drape 100 is described having an adhesive surface 102, a non-adhesive surface 104, and a retraction area 106. Prior to application of the drape 100, the adhesive surface 102 is protected by a protective sheet (not shown) that can be pulled away to expose the adhesive surface 102. The retraction area 106 includes an open area 108 in the non-adhesive surface 104 and two retracting elements, an upper retraction member 110 and a lower retraction member 112, preferably attached to the non-adhesive surface 104 at upper member base 114 and lower member base 116, respectively.

Each retraction member 110,112 includes a non-adhesive extension 118,120, respectively. The non-adhesive extensions 118,120 are preferably rectangular in shape, but may be of varied shape, for example, tapered, trapezoidal, semi-circular, etc. The non-adhesive extensions 118,120, when extended, are preferably of sufficient length to wrap around the lid margin of eyelid 12,16. When folded, as shown in FIG. 4, the non-adhesive extensions 118,120 create a retraction gap 124 between edges 126,128 of the non-adhesive extensions 118,120. Each retracting member 110,112 preferably includes a retraction flap 130,132.

The corresponding upper and lower elements of the drape system of the present invention preferably exhibit similar functionality and structural characteristics. Accordingly, throughout this application the description of an upper element, for example, an upper retraction member 110, an upper non-adhesive extension 118, or an upper retraction flap 130, shall be understood to describe the characteristics of the corresponding lower element.

Figure 5:
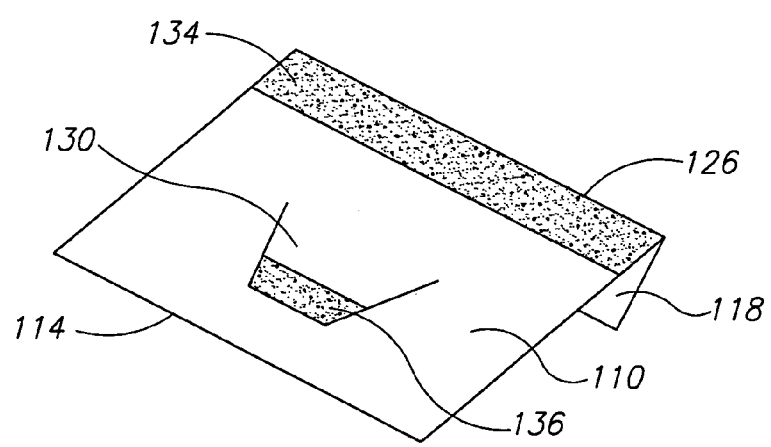
FIG. 5 is an illustration of the underside of a retraction member of the drape system shown in FIG. 4.

As shown with reference to FIG. 5, the underside of the retraction member 110 includes an adhesive portion 134. In addition, the underside of the retraction flap 130 includes an adhesive portion 136. Prior to application of the adhesive portions 134,136, the adhesive portions are protected by material that can be pulled away to expose the adhesive area.

The adhesive portion 136 in these and other embodiments may consist of glue, Velcro (with a corresponding material loop for securing the Velcro connection), button, snap or sliding snap or connection mechanism or other attachment means.

Figure 6:
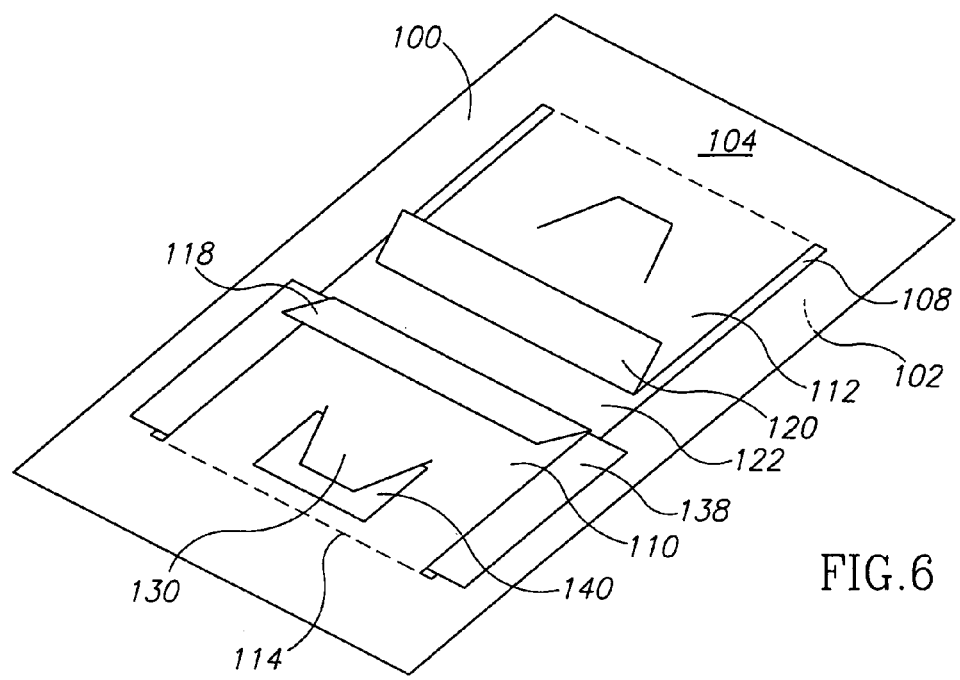
FIG. 6 is an illustration of the drape system shown in FIG. 4, further including protective sheets.

More specifically, with reference to FIG. 6, a protective sheet 138 is present along the underside of the retraction member 110 to prevent premature adhesion by the adhesive portion 134. The protective sheet 138 is preferably made out of a relatively stiff material that is larger than the open area 108 in order to stabilize the retraction member 110 with respect to the open area 108 until application of the adhesive portion 134 of the extension. Alternatively, the protective sheet 138 may be continuous with the larger protective sheet (not shown) which protects the adhesive surface 102 of drape 100, and other means may be used to stabilize the extension during application, for example, removable attachments between the retraction member 110 and the drape 100. A protective sheet 140 is present along the underside of the retraction flap 130 to prevent premature adhesion by the adhesive portion 136. Again, the protective sheet 140 is preferably made out of a relatively stiff material that is larger than the retraction flap 130 in order to stabilize the retraction flap with respect to the retraction member 110 until application of the adhesive portion 136 of the retraction flap.

Figure 7:
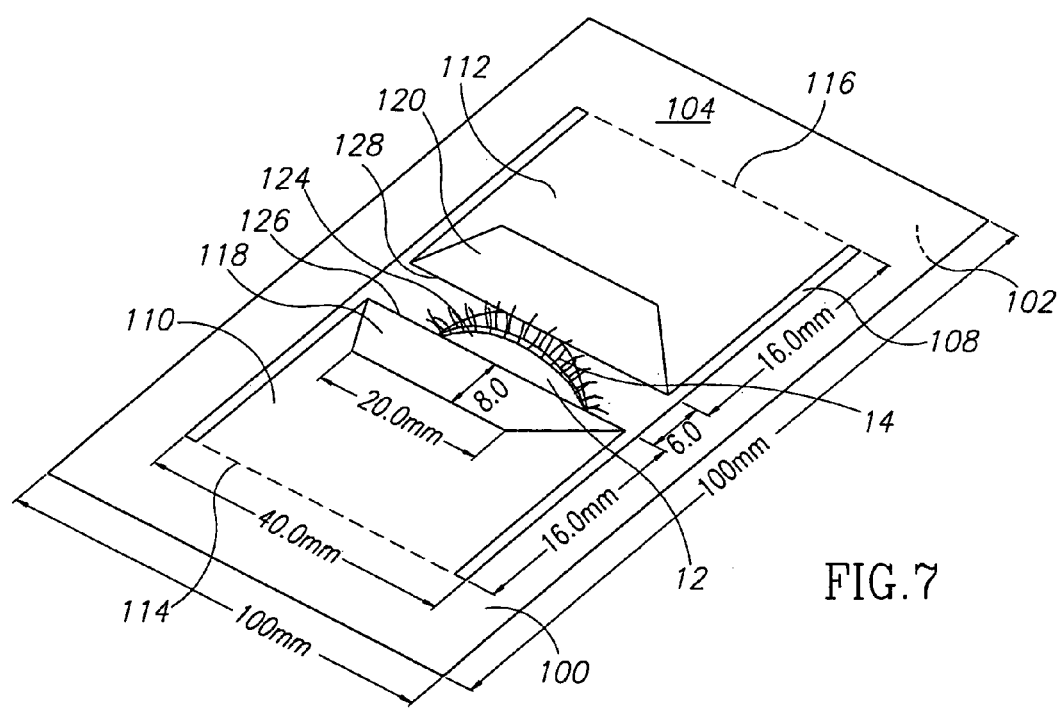
FIG. 7 is an illustration of preferred dimensions for aspects of a drape system in accordance with the invention.
Figure 8:
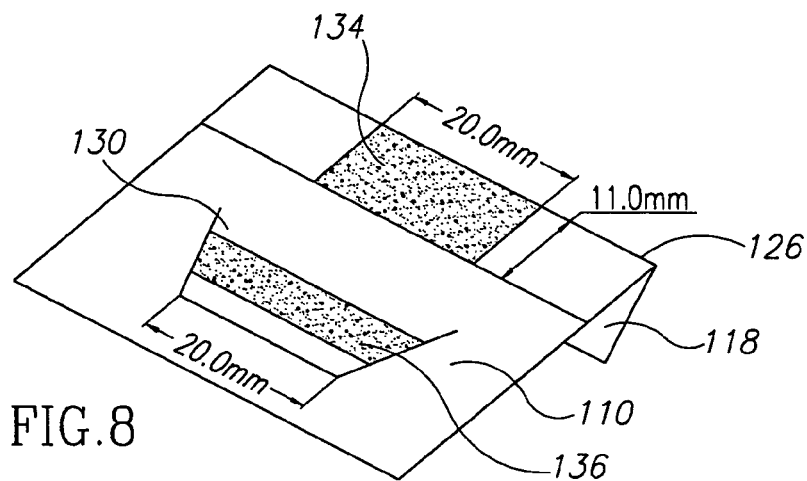
FIG. 8 is an illustration of preferred dimensions for aspects of the underside of a retraction member of a drape system in accordance with the invention.
Figure 9:
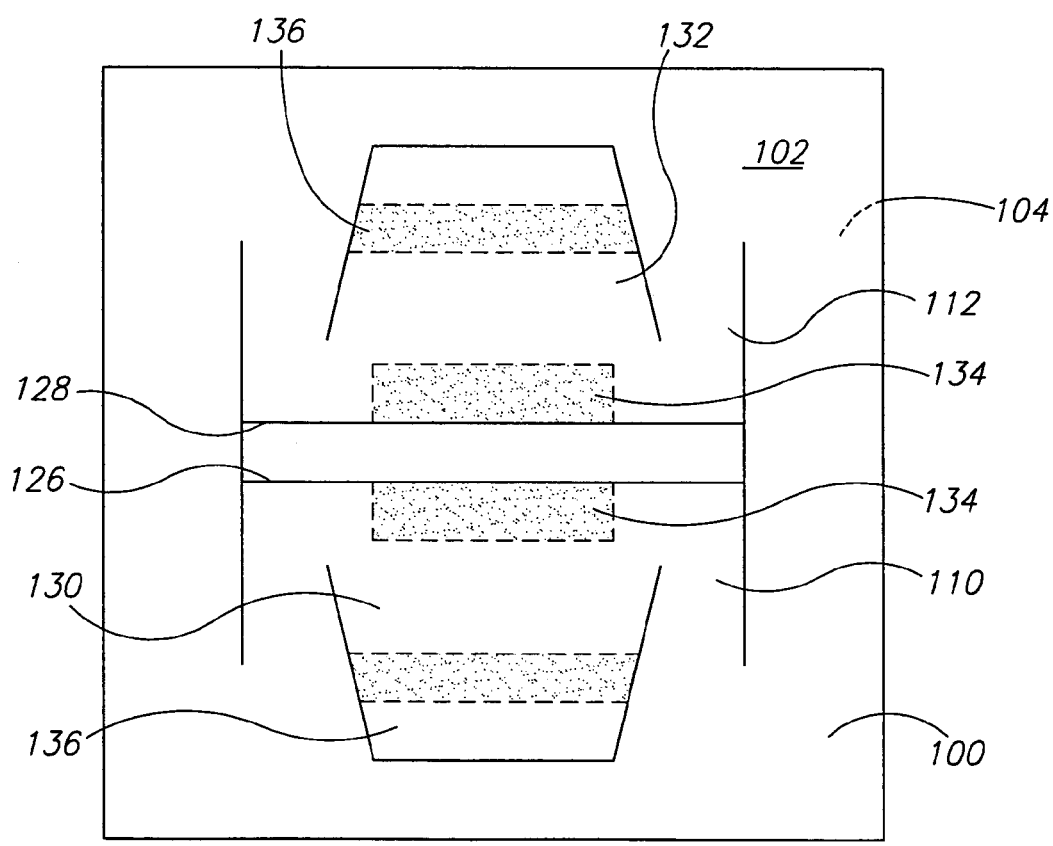
FIG. 9 is an illustration of preferred dimensions for aspects of the underside of a drape system in accordance with the invention.

FIGS. 7–9 show one embodiment of the drape system of the present invention setting forth preferred dimensions for above-described features of the retraction area 106. These specific dimensions are exemplary only and may be varied to meet design, manufacturing or patient criteria without departing from the scope of the present invention. Assuming a 100 mm square section of drape, the retraction area 106 is defined as a rectangle approximately 38 mm long by 40 mm wide. The retraction members 110,112 extend towards each other approximately 16 mm from the upper member base 114 and lower member base 116, respectively. The retraction members 110,112 are folded along edges 126,128 to define the non-adhesive extensions 118,120, respectively, creating a retraction gap 124 of approximately 6 mm between the retraction members 110,112. The non-adhesive extensions 118,120 are approximately 8 mm in length and may vary in width depending on the shape of the non-adhesive extension. As shown with respect to FIG. 7, which illustrates a tapered shape for the non-adhesive extensions 118,120, the width of the non-adhesive extensions is 20 mm.

As better described with reference to FIG. 8, the adhesive portion 134 of the retraction member 110 is preferably centered along the edge 126, approximately 20 mm in width, and extending away from the edge 126 approximately 4 mm.

As better described with reference to FIG. 9, the retraction flap 130 is preferably formed approximately 7 mm from the edge 126 of the non-adhesive extension 118. The length of the retraction flap 130 is approximately 16 mm. The width of the retraction flap 130 at their tapered-most edge is approximately 20 mm. The width of the retraction flap 130 at their tapered-most edge preferably corresponds to the width of the adhesive portion 134 to facilitate even pull along the eyelid during application of the drape system. In a preferred embodiment, the adhesive portion 136 of the retraction flap 130 is removed from the tapered edge of the retraction flaps to allow the surgeon to manipulate the retraction flaps without prematurely engaging the adhesion.

Figure 10:
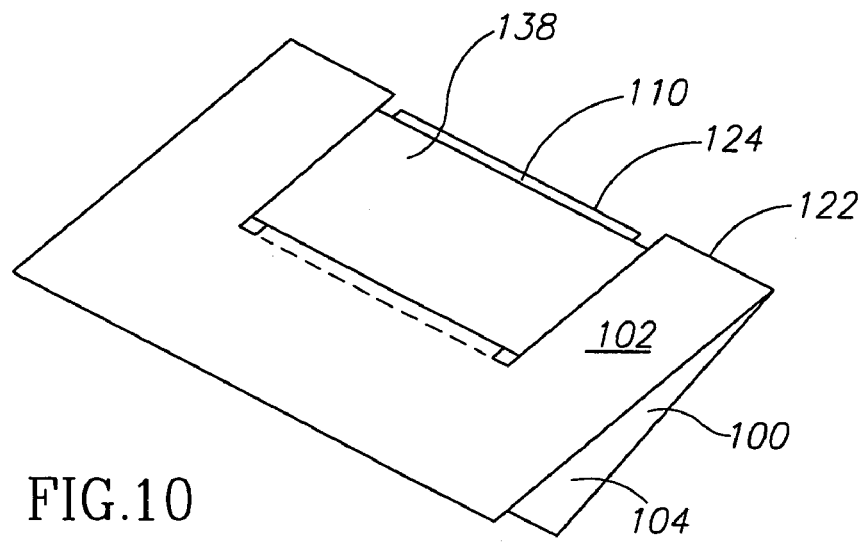
FIG. 10 is an illustration of a folded drape system in accordance with the invention.

For purposes of storage, packaging, display and transportation, and prior to application, the draping system of the present invention may be folded either horizontally or vertically. In one embodiment, as shown with reference to FIGS. 4 and 10, the drape 100 is folded along the midway point 122 of the retraction area 106 such that the retraction gap 124 between edges 126,128 of the non-adhesive extensions 118,120 is preserved. Alternatively, the drape 100 may be folded lengthwise along the midpoint (not shown) of the retraction area 106.

Figure 11:
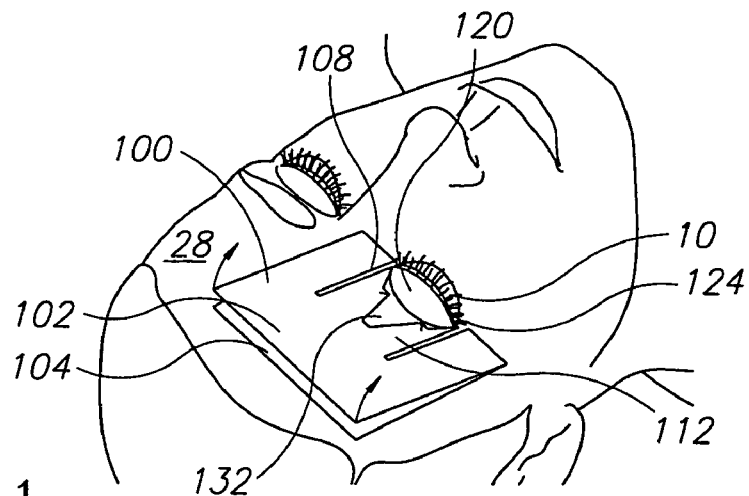
FIG. 11 is an illustration of a drape system in accordance with the invention wherein the drape is folded and applied to a patient's face from a horizontal configuration.
Figure 12:
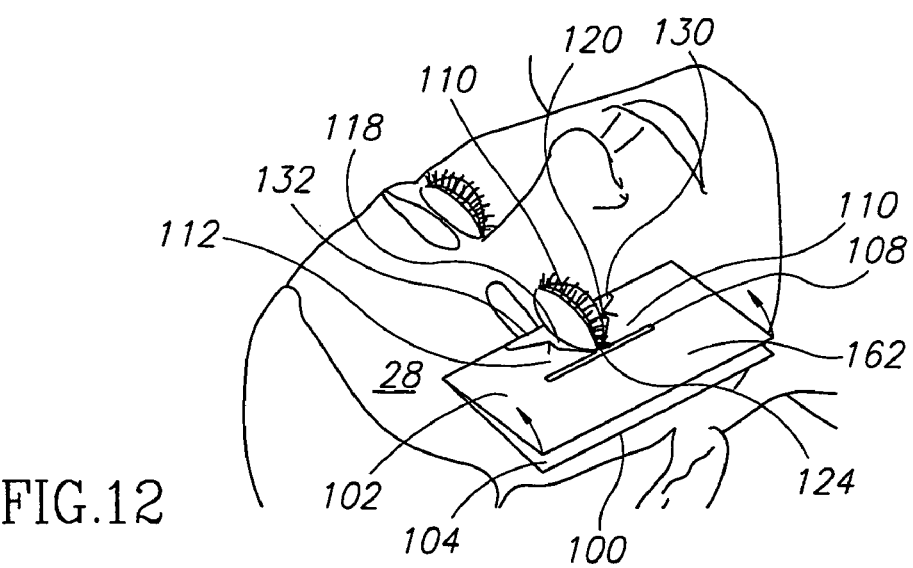
FIG. 12 is an illustration of a drape system in accordance with the invention wherein the drape is folded and applied to a patient's face from a vertical configuration.

The method of application of the embodiment of the drape system described above is as follows. Prior to application of the drape 100, the drape system is removed from its storage location or packaging. Depending on the manner in which it is stored or packaged, the drape system will initially be folded in either a horizontal or vertical configuration. Initially, the protective sheet (not shown) covering the adhesive surface 102 of the drape 100 is removed. In a preferred embodiment, the protective sheet would consist of two halves to facilitate the ease of application. The application of the drape begins with the patient's eye 10 closed. The adhesive surface 102 is applied to the facial area 28 around the eye 10. As shown with respect to FIGS. 11 and 12, a surgeon will typically apply the drape either from the top or the side of the patient's head. FIG. 11 shows one example of how a drape folded in a horizontal configuration may be positioned and applied. FIG. 12 shows one example of how a drape folded in a vertical configuration may be positioned and applied. In either case, the surgeon uses the retraction gap 124 in the retraction area 106 to align the patient's eye. In the single-fold embodiment shown, one half of the folded drape is aligned and applied, after which the second half of the drape is aligned and applied. Alternative embodiments may include drapes folded more than once, in which case multiple folded drape sections may be aligned and applied.

Figure 13:
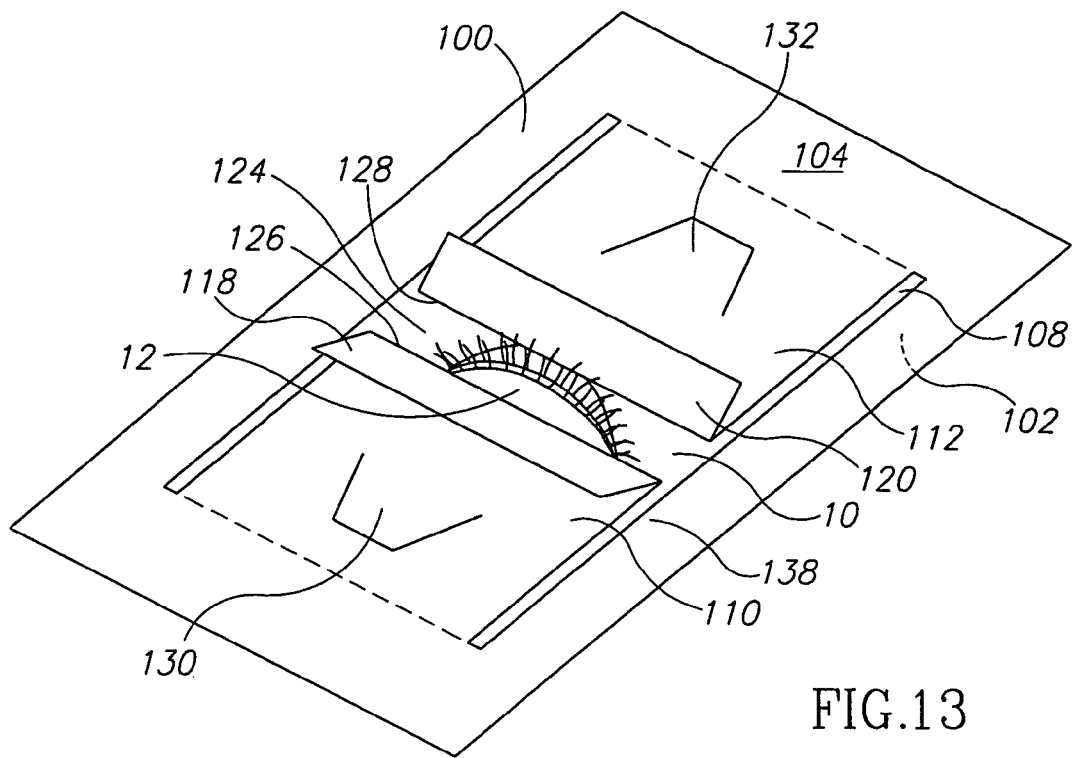
FIG. 13 is an illustration of a drape system in accordance with the invention being applied around a patient's eye.

More specifically, with reference to FIG. 13, the drape 100 is positioned around the eye such that the upper eyelid 12 with upper eyelashes 14 and a lower eyelid 16 having lower eyelashes 18 of the eye 10 is exposed through the retraction gap 124 between edges 126,128 of the non-adhesive extensions 118,120.

The protective sheet 138 corresponding to the retraction member 110 is removed, exposing the adhesive portion 134 along the underside of the retraction member 110. The adhesive portion 134 of the retraction member 110 is applied to the facial surface along the upper eyelid 12. This step is repeated for the protective sheet 138 corresponding to the retraction member 112. The protective sheet 138 is removed, exposing the adhesive portion 134 along the underside of the retraction member 112. The adhesive portion 134 of the retraction member 112 is applied to the facial surface along the lower eyelid 16.

The protective sheet 140 corresponding to the retraction flap 130 is removed and the retraction flap is pulled in a direction away from the eye 10 to pull open the upper eyelid 12. The adhesive portion 136 along the underside of the retraction flap 130 is applied to the drape 100 to secure the upper eyelid in its retracted position. This step is repeated for the protective sheet 140 corresponding to the retraction flap 132. The protective sheet 140 corresponding to the retraction flap 132 is removed and the retraction flap is pulled in a direction away from the eye 10 to pull open the lower eyelid 16. The adhesive portion 136 along the underside of the retraction flap 132 is applied to the drape 100 to secure the lower eyelid in its retracted position.

In the preferred embodiment, the adhesive portion 134 of both retraction members 110,112 is applied before the upper and lower eyelids are retracted. The adhesive portion 134 of the retraction member 110 may be applied and the corresponding upper eyelid 12 retracted and secured using the retraction flap 130 prior to application of the adhesive portion 134 of the retraction member 112 and retraction of the corresponding lower eyelid 16. Alternatively, the adhesive portion 134 of the retraction member 112 may be applied and the corresponding lower eyelid 16 retracted and secured using the retraction flap 132 prior to application of the adhesive portion 134 of the retraction member 110 and retraction of the corresponding lower eyelid 12.

Figure 14:
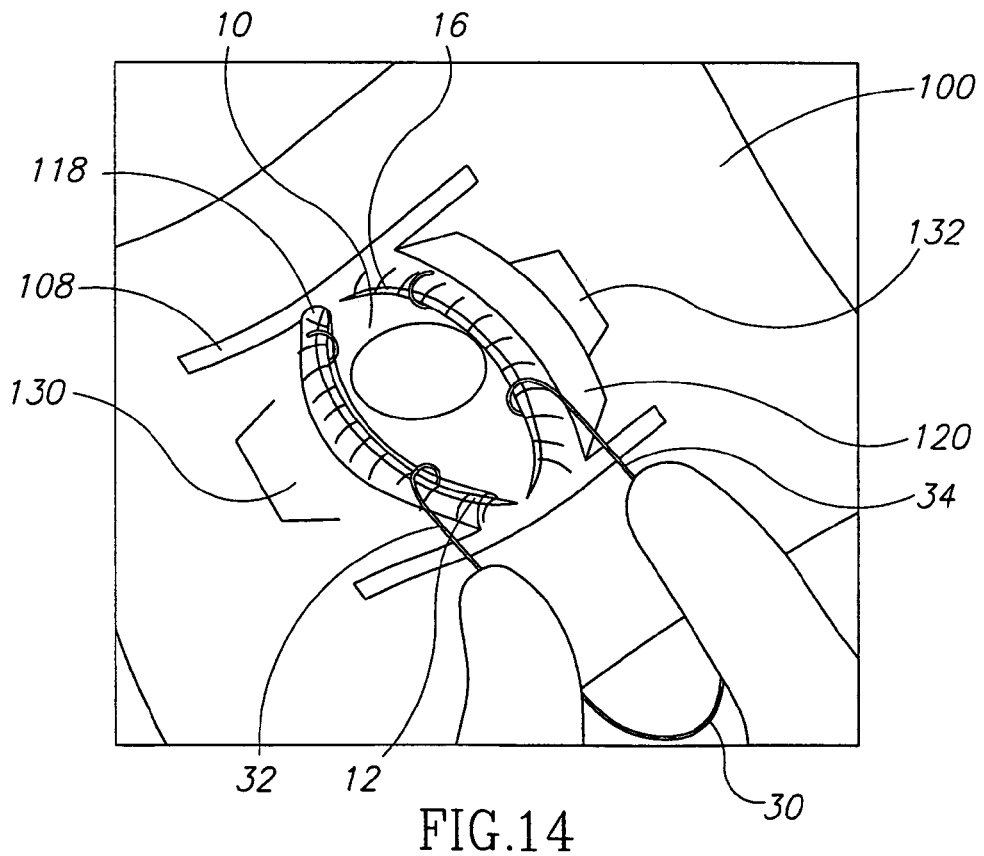
FIG. 14 is an illustration of a speculum used with a drape system in accordance with the invention, the speculum being applied to retract a patient's upper eyelid.

The non-adhesive extensions 118,120 of the retraction members 110,112 are tucked underneath the retracted upper eyelid 12 and lower eyelid 16, respectively. This may occur in any order. A retractable eyelid speculum 30 having an upper arm 32 and a lower arm 34 is used to hold the eyelids open and to maintain the non-adhesive extensions 118,120 tucked underneath the retracted upper and lower eyelids. In one embodiment, shown with reference to FIG. 14, the non-adhesive extension 118 is folded around and tucked underneath the retracted upper eyelid 12 and held in place, in the retracted position, by the upper arm 32 of the speculum 30. The process is repeated with respect to the lower eyelid 16, wherein the non-adhesive extension 120 is folded around and tucked underneath the retracted lower eyelid 16 and held in place, in the retracted position, by the lower arm 34 of the speculum 30. Maintaining the non-adhesive extensions 118,120 around the upper and lower eyelids 12,16 and corresponding upper and lower eyelashes 14,18 reduces potential interference with the surgery by the lids and eyelashes and keeps the surgical area clear of potential debris and bacteria from the lid margin and eyelashes.

The drape 100 is maintained in place with relation to the eye 10 by the adhesive surface 102. The adhesive portions 134,136 together maintain the eyelids in a retracted state. In this embodiment, in addition to maintaining the non-adhesive extensions 118,120 folded around the lids and eyelashes, the speculum 30 further serves to maintain the lids in a retracted state.

Alternative configurations of the non-adhesive extensions 118,120 are contemplated and described below. Modifying the non-adhesive extensions to more securely hold the eyelid in a retracted position to reduce or eliminate the necessity of an eyelid speculum. While only embodiments describing one of the non-adhesive extensions 118,120 are described, these alternative systems are equally applicable to both non-adhesive extensions.

Figure 15:
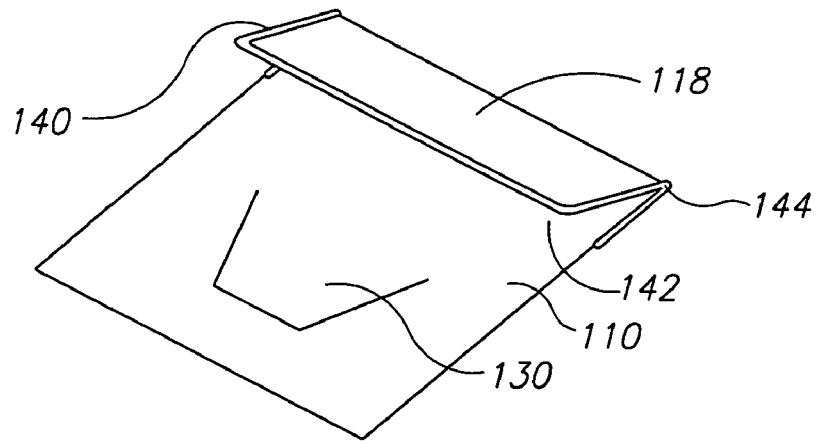
FIG. 15 is an illustration of a drape in accordance with the invention wherein a non-adhesive extension includes a small wire or other rigid but malleable material.

In one such embodiment, shown in FIG. 15 with reference to the non-adhesive extension 118, the non-adhesive extension includes a small wire or other rigid but malleable material 140 nonabrasively embedded along the non-adhesive extension edges 142 and partially along the adjoining edge of the retraction member 110. When the non-adhesive extension 118 is folded around and tucked underneath the retracted upper eyelid 12, the wires are folded as well, and in holding their newly folded shape maintain the non-adhesive extension 118 folded around the eyelids and eyelashes.

Figure 16:
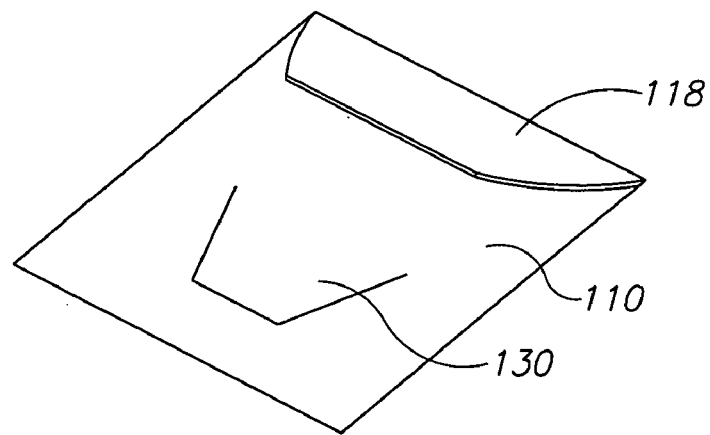
FIG. 16 is an illustration of a drape system in accordance with the invention wherein a non-adhesive extension is formed of a firm plastic or other substantially rigid material.

In yet another embodiment, shown in FIG. 16 with reference to the non-adhesive extension 118, the non-adhesive extension is formed of a firm plastic or other substantially rigid material. The action of folding the rigid non-adhesive extension 118 around and tucking it underneath the retracted upper eyelid 12 lodges the rigid non-adhesive extension under the eyelid where it is unable to independently dislodge from under the eyelid, thereby securely maintaining the eyelids and eyelashes in the retracted position.

Figure 17:
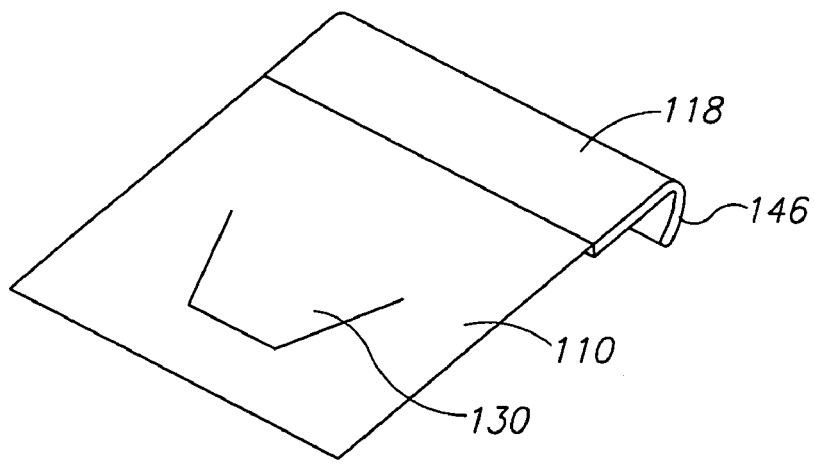
FIG. 17 is an illustration of a drape system in accordance with the invention wherein a non-adhesive extension is formed of a plastic or other substantially rigid material in the shape of a hook.

In an alternative embodiment, the shape of the non-adhesive extension is altered to mirror the functionality of an eyelid speculum. In one example, shown in FIG. 17 with reference to the non-adhesive extension 118, the non-adhesive extension is formed of a plastic or other substantially rigid material in the shape of a hook 146. In this embodiment, as the retraction flap 130 pulls the lower eyelid 12 and lower eyelashes 14 away from the eye 10, the hook 146 of the non-adhesive extension 118 engages and captures the lower eyelid and eyelashes, retracting them away from the eye and maintaining them in a retracted position by virtue of the strength of the rigid hook 146.

Further alternative embodiments of the present invention exist that eliminate the need for an external eyelid speculum to hold the eyelids open and to maintain the non-adhesive extensions 118,120 folded around the eyelids and eyelashes. Such embodiments involve initial retraction of the eyelid in order to apply a speculum action member, after which the speculum action member is used to independently retract and secure the eyelid and eyelashes. In these embodiments there is preferably relative movement between the device used to initially retract the eyelid and the speculum action member. This relative movement facilitates both the application of the speculum action member and the subsequent movement of the speculum action member. Many such alternative embodiments also provide additional benefits, such as the reduction of surgeon manipulation required to apply the drape or an increase in sterilization protection.

Figure 18:
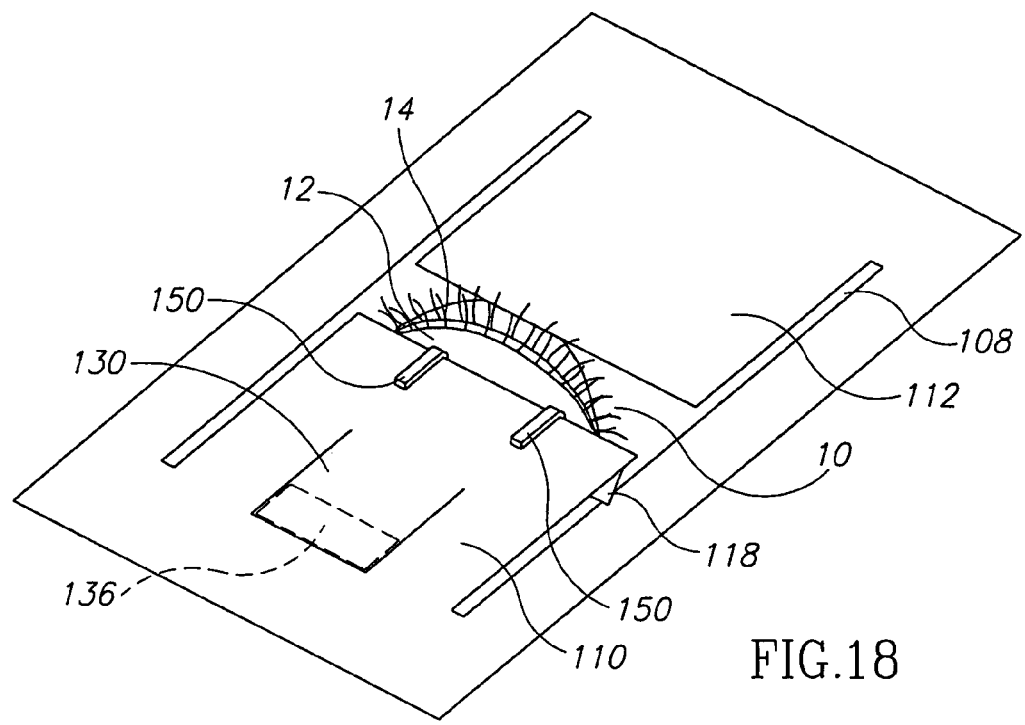
FIG. 18 is an illustration of a drape system in accordance with the invention wherein hooks as a speculum action members.

FIG. 18 illustrates an alternative embodiment using hooks as speculum action members. In this embodiment, a plurality of hooks 150 are attached to the retraction member 110 and non-adherent extension 118. In a preferred application, a surgeon inserts one sterilized finger or tool (not shown) under the retraction flap 130 and directly retracts the eyelid 12. Once the eyelid and eyelashes have cleared the hooks 150, the surgeon uses a sterilized hand or other tool (not shown) to engage the hooks 150 and non-adherent extension 118 around the eyelid 12. The retraction flap 130 is then pulled away from the eye 10, which causes the hooks 150 and non-adherent extension 118 and, correspondingly, the eyelid 12 and eyelashes 14 secluded therein, to retract. The adherent portion 136 on the underside of the retraction flap 130 is applied to the non-adhesive surface 104 of the drape 100 to secure the retraction flap 118, the hooks 150 and non-adherent extension 118, and the eyelid 12 and eyelashes 14 in a retracted position. This process may be repeated for the corresponding lower elements of the drape system.

Figure 19:
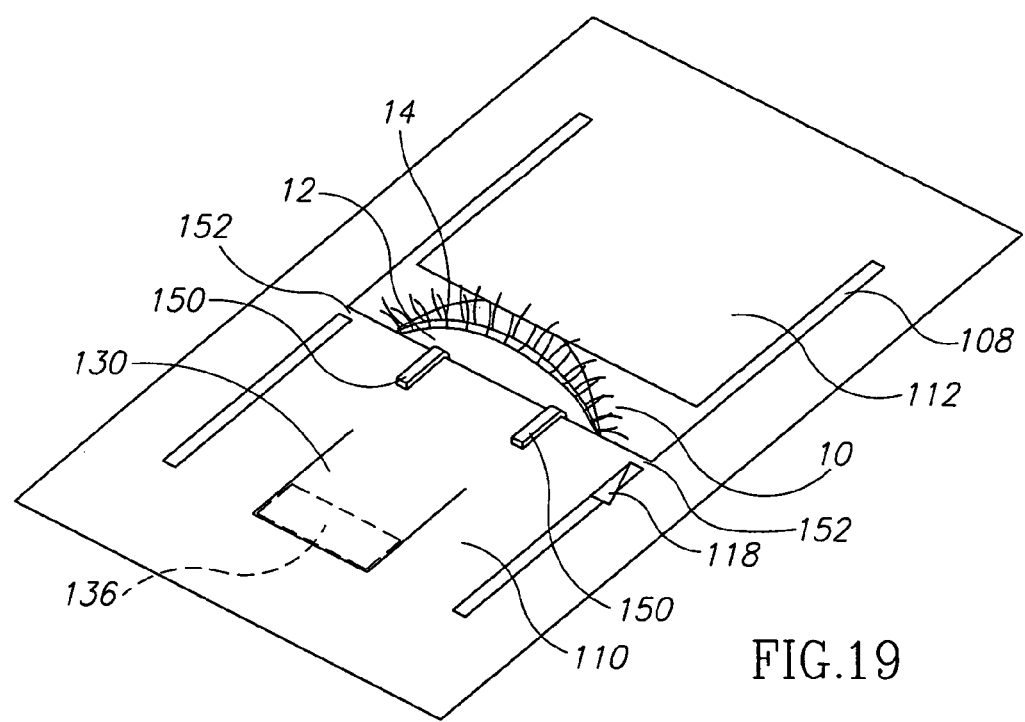
FIG. 19 is an illustration of the drape system shown in FIG. 18, further including bridging elements.

FIG. 19 illustrates an alternative embodiment of the drape system described above with reference to FIG. 18. This embodiment incorporates the use of bridging elements to maintain the retraction members 110,112 in position within the retraction area 106 until retraction of the eyelids occurs. The bridging elements are preferably made of the drape material and formed during creation of the drape system. The bridging elements are preferably formed of a thin, strip material that is easily broken upon application of a degree of force. Alternatively, the bridging elements may be made of any type of connectable material independent of the creation of the other aspects of the drape system. In an alternative embodiment (not shown), the bridging elements maintain the retraction members 110,112 in position within the retraction area 106 via other connections, for example, connections between the extension flaps 118,120 rather than between the retraction members 110,112 and the drape 100. The bridging elements may be incorporated into many of the alternative drape systems described herein.

As shown in FIG. 19, bridging elements 152 preferably extend between the edge 126 of the retraction member 110 and the drape. As the surgeon inserts one sterilized finger or tool (not shown) under the retraction flap 130 and directly retracts the eyelid 12, the bridging elements 152 maintain the retraction member 110 in place with respect to the eye 10. As the retraction flap 130 is pulled away from the eye 10, causing the hooks 150 and non-adherent extension 118 and, correspondingly, the eyelid 12 and eyelashes 14 secluded therein, to retract, the bridging elements 152 are broken, allowing the retraction flap 130 to be retracted. This process may be repeated for the corresponding lower elements of the drape system.

Figure 20:
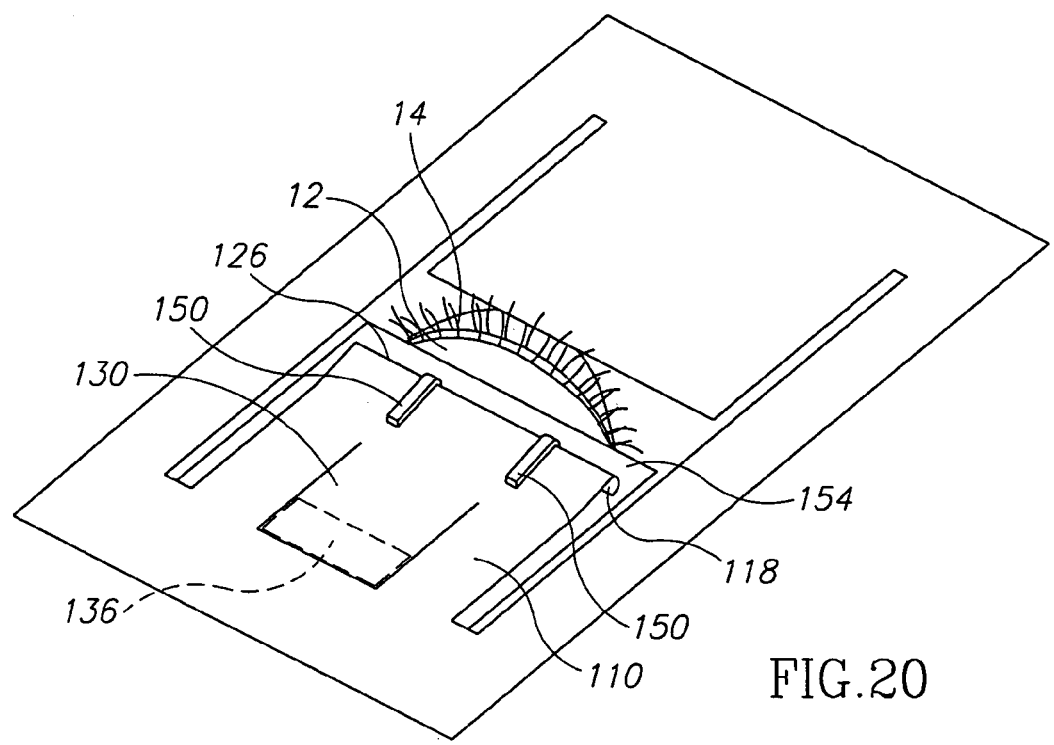
FIG. 20 is an illustration of a drape system in accordance with the invention that incorporates the use of a self-adherent retraction member underneath the retraction member.

FIG. 20 illustrates an alternative embodiment of the drape system that eliminates the need for a surgeon to directly contact the patient's skin during application. This embodiment incorporates the use of a self-adherent retraction member 154 that lies underneath the retraction member 110 and extends towards the eye 10 beyond the edge 126 of the non-adherent extension 118. When the drape is applied, the self-adherent retraction member 154 is adhered to the upper eyelid 12. Subsequently during the application of the drape system, a surgeon inserts a finger or tool (not shown) under the retraction flap 130 and retracts the eyelid 12, this time by pulling the self-adherent retraction member 154 and the upper eyelid 12 and eyelashes 14 away from the eye 10. Once the eyelid and eyelashes have cleared the hooks 150, the surgeon uses a sterilized hand or other tool (not shown) to engage the hooks 150 and non-adherent extension 118 around the eyelid 12. The retraction flap 130 is then pulled away from the eye 10, which causes the hooks 150 and non-adherent extension 118 and, correspondingly, the eyelid 12 and eyelashes 14 secluded therein, to retract. The adherent portion 136 on the underside of the retraction flap 130 is applied to the non-adhesive surface 104 of the drape 100 to secure the retraction flap 118, the hooks 150, the non-adherent extension 118 and the eyelid 12 and eyelashes 14 in a retracted position. This process may be repeated for the corresponding lower elements of the drape system.

Figure 21:
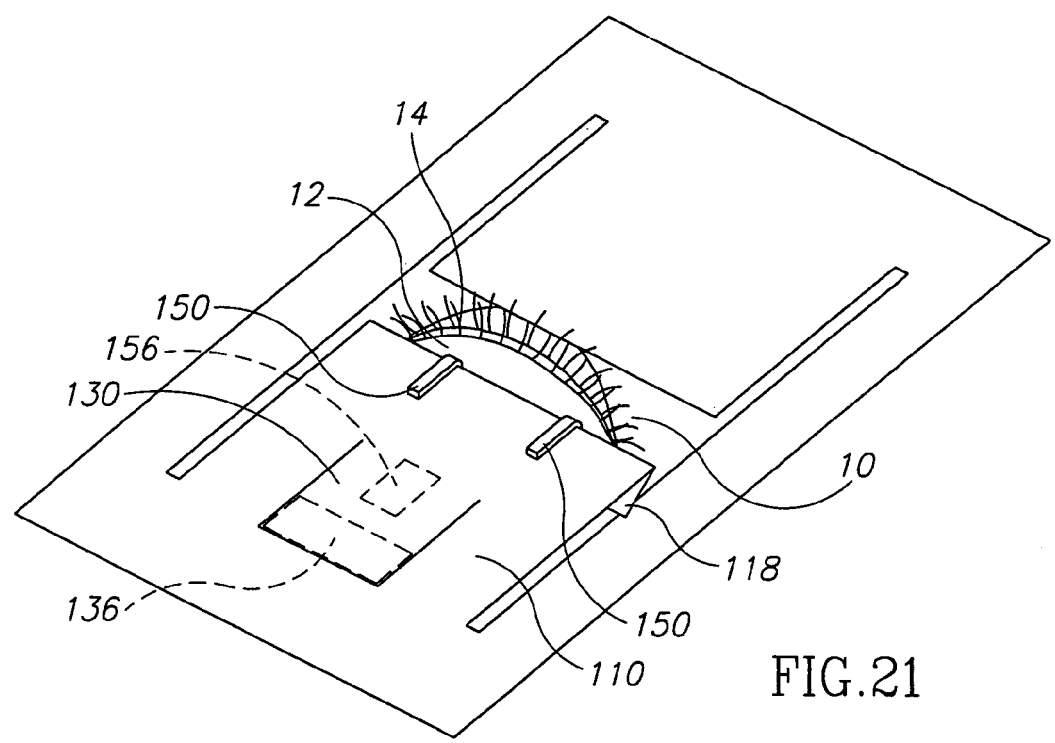
FIG. 21 is an illustration of a drape system in accordance with the invention that incorporates the use of a self-adherent area located underneath the a retraction member.

FIG. 21 illustrates an alternative embodiment of the drape system that eliminates the need for a surgeon to directly contact the patient's skin during application, this time by taking advantage of the inherent elasticity of the drape and the close positioning of the hooks 150 to the eyelid 12, and the more remote position of the adhesive area 156 in relation to the hooks 150, to allow for relative movement between the adhesive area 156 and hooks 150. This embodiment incorporates the use of a self-adherent area 156 that lies underneath the retraction member 110. During the application of the drape system, a surgeon applies pressure to the self-adherent area 156, adhering the retraction member 110 to the facial area 28 above the eyelid 12. While pulling the retraction flap 130 away from the eye 10, the surgeon pulls the hooks 150 in the opposite direction towards the eyelid 12, thus causing the drape to stretch sufficiently to allow the hooks 150 and non-adherent extension 118 to wrap around the lid margin. The retraction flap 130 is then pulled away from the eye 10, which causes the hooks 150 and non-adherent extension 118 and, correspondingly, the eyelid 12 and eyelashes 14 secluded therein, to retract. The adherent portion 136 on the underside of the retraction flap 130 is applied to the non-adhesive surface 104 of the drape 100 to secure the retraction flap 118, the hooks 150, the non-adherent extension 118 and the eyelid 12 and eyelashes 14 in a retracted position. This process may be repeated for the corresponding lower elements of the drape system.

Figure 22:
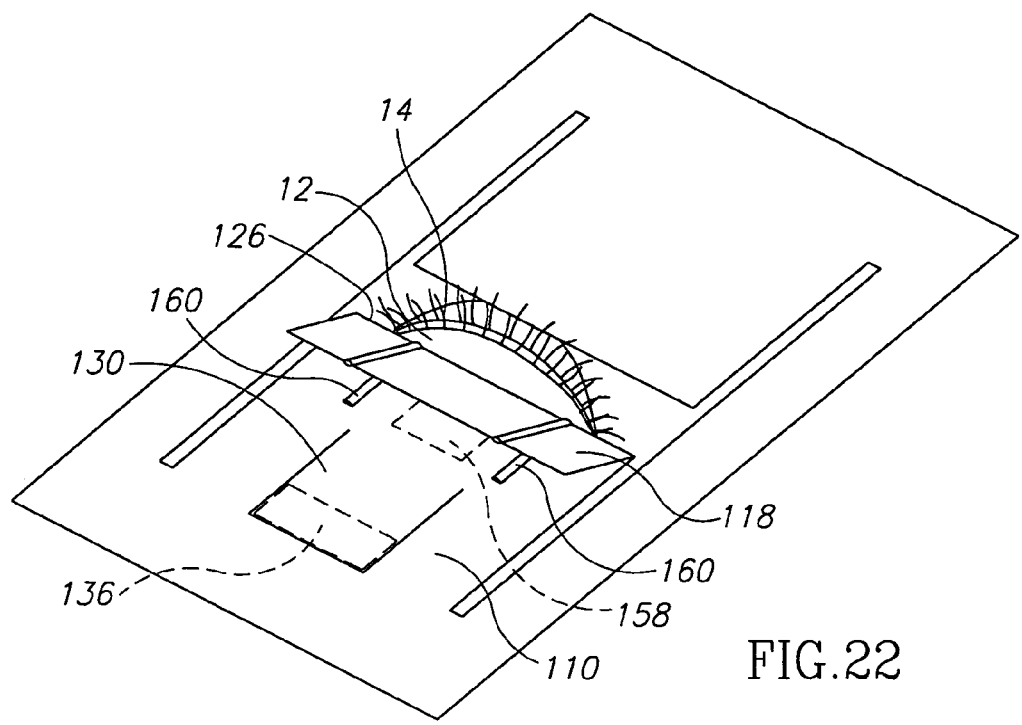
FIG. 22 is an illustration of a drape system in accordance with the invention that incorporates the use of a self-adherent area that lies underneath a retraction member as well as the use of malleable shafts affixed to the retraction member.

FIG. 22 illustrates an alternative embodiment of the drape system that eliminates the need for a surgeon to directly contact the patient's skin during application. This embodiment incorporates the use of a self-adherent area 158 that lies underneath the retraction member 110 as well as the use of malleable shafts 160 affixed to the retraction member 110. During the application of the drape system, a surgeon applies pressure to the self-adherent area 158, adhering the retraction member 110 to the facial area 28 on or above the eyelid 12. Pulling the retraction member 110 away from the eye 10 retracts the eyelid 12 away from the eye, allowing room for the surgeon to bend the shafts 160 into a hook configuration around the eyelid 12 that engages the non-adherent extension 118 around the eyelid 12 and eyelashes 14. The retraction flap 130 is then pulled away from the eye 10, which causes the shafts 160 and non-adherent extension 118 and, correspondingly, the eyelid 12 and eyelashes 14 secluded therein, to retract. The natural elasticity of the skin allows for relative movement between the hooks 150 and adhesive area 158 such that the hooks 150 rather than adhesive area 158 bear the load of securing the lids. The adherent portion 136 on the underside of the retraction flap 130 is applied to the non-adhesive surface 104 of the drape 100 (not shown) to secure the retraction flap 118, the shafts 160, the non-adherent extension 118 and the eyelid 12 and eyelashes 14 in a retracted position. This process may be repeated for the corresponding lower elements of the drape system.

Figure 23:
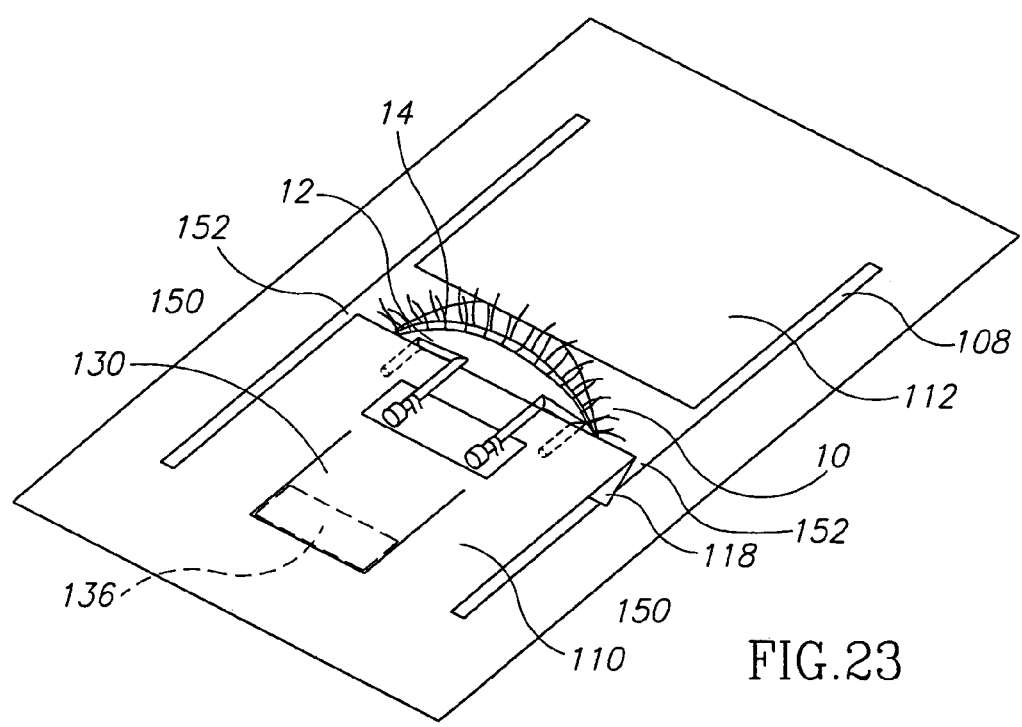
FIG. 23 is an illustration of a drape system in accordance with the invention that incorporates rotatable "J" shaped rods used to form hooks used to retract a patient's eyelid, wherein the rods are in a retracted configuration.
Figure 24:
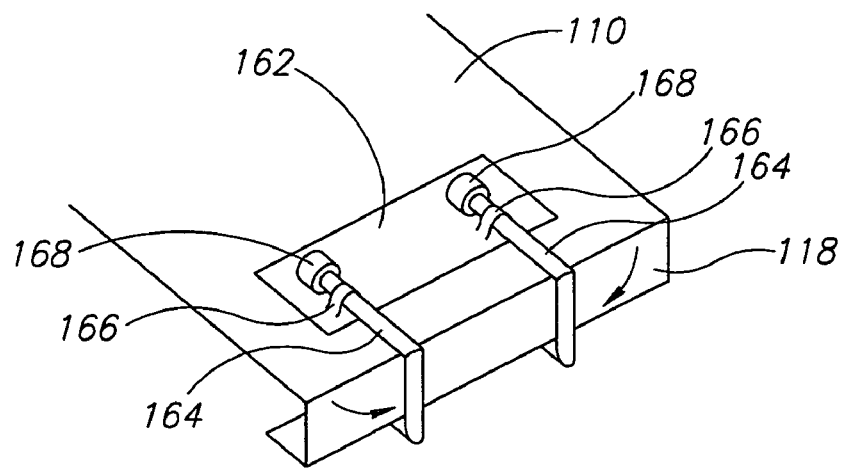
FIG. 24 is an illustration of the rod assembly of the drape system shown in FIG. 23, wherein the rods are in an extended, hook configuration.

FIGS. 23 and 24 illustrate an alternative embodiment of the drape system described with reference to FIG. 18. The retraction member 110 includes a substantially rigid plate 162 to which are preferably attached "J" shaped rods 164. These rods are attached to the plate 162, preferably using connectors 166, in a manner that allows the rods 164 to rotate. The rods 164 are preferably prevented from pulling through the connectors 166 by rod heads 168 located at one end of the rods 164. As shown with further reference to FIG. 24, during application of the drape system, the rods 164 are rotated to lie underneath the non-adhesive extension 118 of the retraction member 110. This position forms hooks that are in position to engage the eyelid.

During the application of this embodiment of the drape system, a surgeon inserts a finger or tool (not shown) under the retraction flap 130 and retracts the eyelid 12. The surgeon rotates the rods 164 into a more vertical alignment, thereby engaging the non-adherent extension 118 around the eyelid 12 and eyelashes 14. The retraction flap 130 is then pulled away from the eye 10, which causes the rods 164 and non-adherent extension 118 and, correspondingly, the eyelid 12 and eyelashes 14 secluded therein, to retract. The adherent portion 136 on the underside of the retraction flap 130 is applied to the non-adhesive surface 104 of the drape 100 (not shown) to secure the retraction flap 118, the rods 164, the non-adherent extension 118 and the eyelid 12 and eyelashes 14 in a retracted position. This process may be repeated for the corresponding lower elements of the drape system.

The embodiment incorporating the use of rotating rods carries a further advantage in that it allows potentially greater compaction of the drape system. Depending on the embodiment, the incorporation of a speculum action member adds bulk to the drape system. The use of rotating rods as described above allows orientation of the speculum action member in a flat configuration that facilitates folding, packaging and transportation of the drape assembly. Other embodiments might include a variety of pre-formed members which can be moved such that a speculum action member is created.

Figure 25:
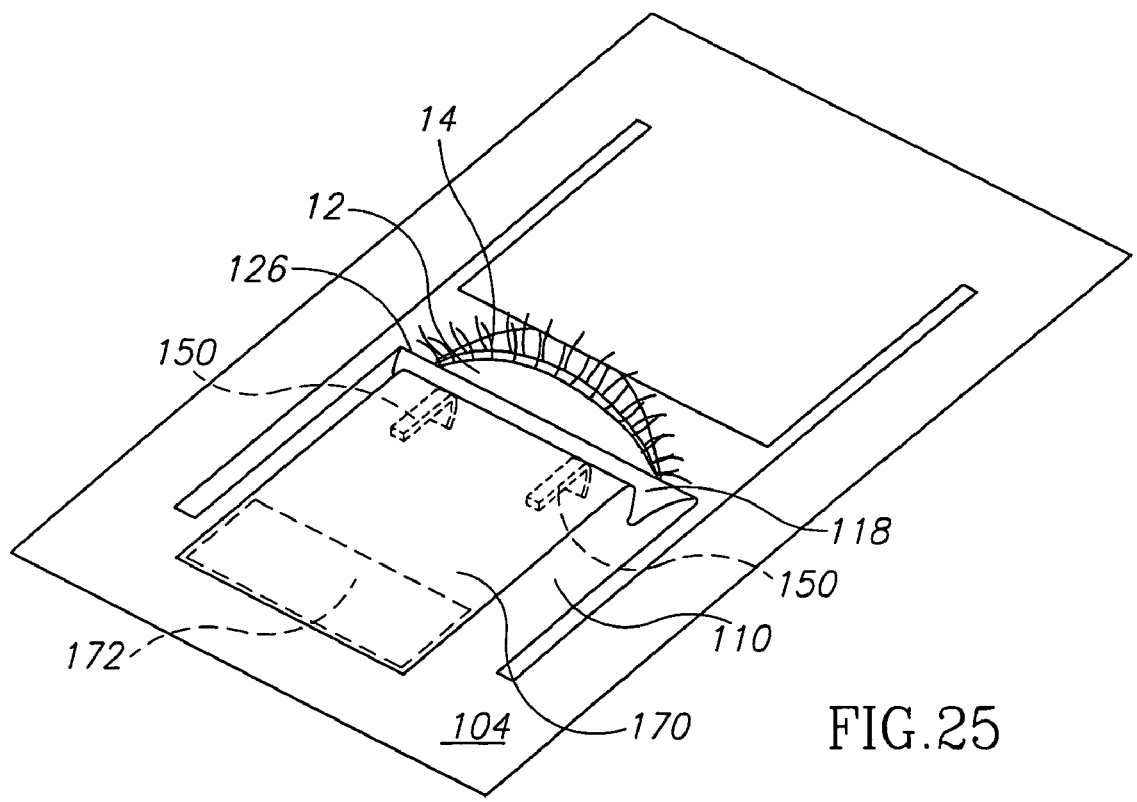
FIG. 25 is an illustration of a drape system in accordance with the invention that incorporates an additional hook extension along with the hooks as a continuation of a non-adherent extension of a retraction member.

FIG. 25 illustrates an alternative embodiment of the drape system that incorporates an additional hook extension 170 along with the hooks 150 as a continuation of the non-adherent extension 118 of the retraction member 110. A surgeon applies pressure to the retraction member 110 underneath the hook extension 170 in close proximity to the eyelid 12, pulling the retraction member 110 away from the eye 10 and retracting the eyelid 12. The surgeon then engages the hooks 150 and non-adherent extension 118 around the eyelid 12 and eyelashes 14. The hook extension 170 is then pulled away from the eye 10, which causes the hooks 150 and non-adherent extension 118 and, correspondingly, the eyelid 12 and eyelashes 14 secluded therein, to retract. An adherent portion 172 on the underside of the hook extension 170 is applied to the non-adhesive surface 104 of the drape 100 to secure the hook extension 170, the hooks 150, non-adherent extension 118 and the eyelid 12 and eyelashes 14 in a retracted position. This process may be repeated for the corresponding lower elements of the drape system.

FIGS. 26–31 illustrate alternative embodiments of the drape system that eliminate the need for an external eyelid speculum, in part by taking advantage of the inherent elasticity of the drape and the close positioning of the non-adherent extension 118 to the eyelid 12.

Figure 26:
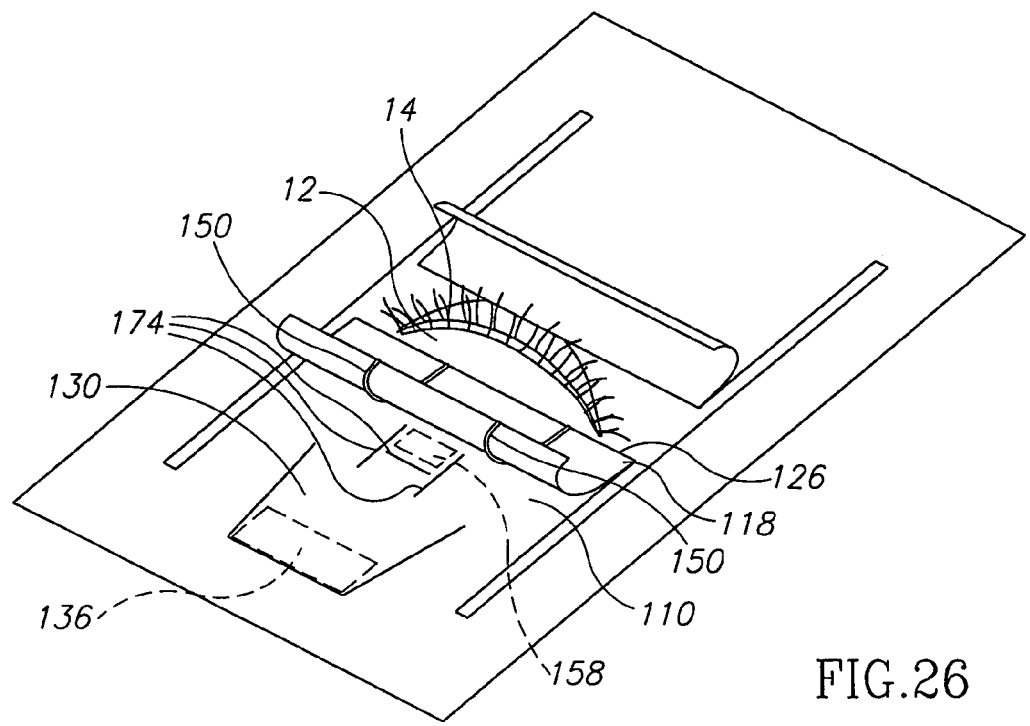
FIG. 26 is an illustration of a drape system in accordance with the invention that incorporates the use of a self-adherent area that lies underneath a retraction member as well as several non-continuous cuts between the self-adherent area and the retraction flap.
Figure 27:
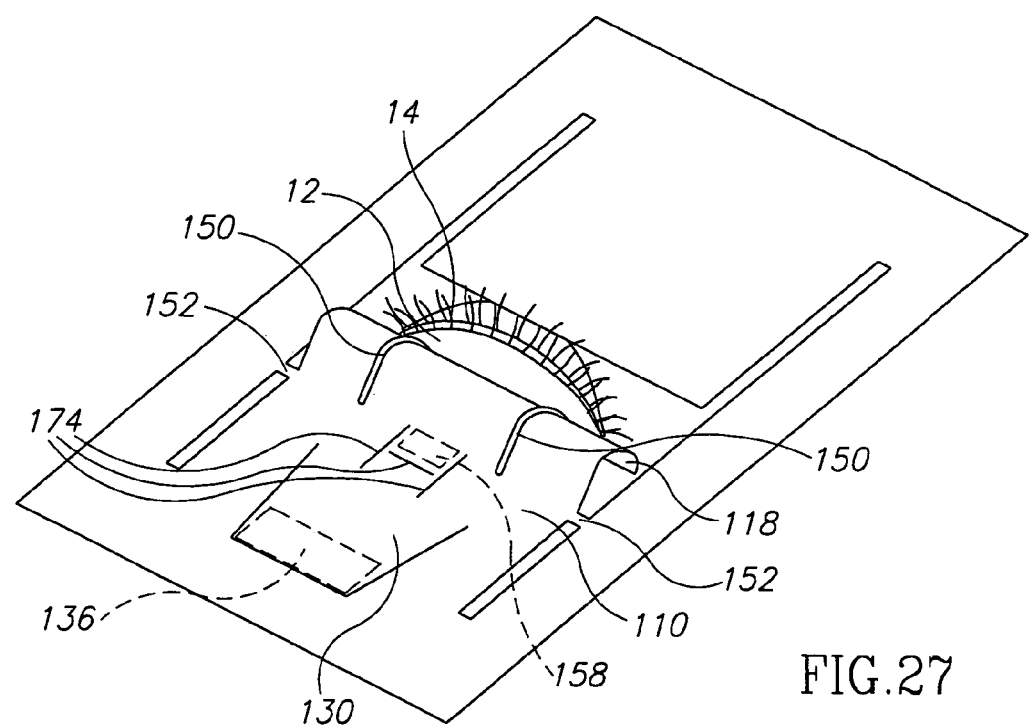
FIG. 27 is an illustration of the drape system shown in FIG. 26, further including bridging elements.

The embodiments shown in FIGS. 26 and 27 incorporates the use of a self-adherent area 158 that lies underneath the retraction member 110 as well as several preferably non-continuous cuts 174 between the self-adherent area 158 and the retraction flap 130. The cuts assist in ensuring that there exists differential movement as between the self-adherent area 158 and the hooks 150 when the retraction flap 130 is pulled to retract the eyelid 12 and eyelashes 14. During the application of the drape system, a surgeon applies pressure to the self-adherent area 158, adhering the retraction member 110 to the facial area 28 on or above the eyelid 12. The surgeon then pulls on retraction flap 130 to partially retract the eyelid 12 away from the eye 10. The non-adherent extension 118 and hooks 150 are unfolded toward the eye and the surgeon wraps them around the partially retracted eyelid 12. As the surgeon continues to pull on the retraction flap 130, the non-continuous cuts 174 stretch apart, relaxing the forces on the self-adherent area 158 and allowing the hooks 150, the non-adherent extension 118 and the eyelid 12 and eyelashes 14 to easily retract and be maintained in the retracted position. The adherent portion 136 on the underside of the retraction flap 130 is applied to the non-adhesive surface 104 of the drape 100 (not shown) to secure the retraction flap 118, the non-adherent extension 118 and the eyelid 12 and eyelashes 14 in a retracted position. This process may be repeated for the corresponding lower elements of the drape system. FIG. 27 illustrates the same drape system described with reference to FIG. 26, further incorporating the use of a bridging element to maintain the retraction member 110 in position within the retraction area 106 until retraction of the eyelids occurs.

Figure 28:
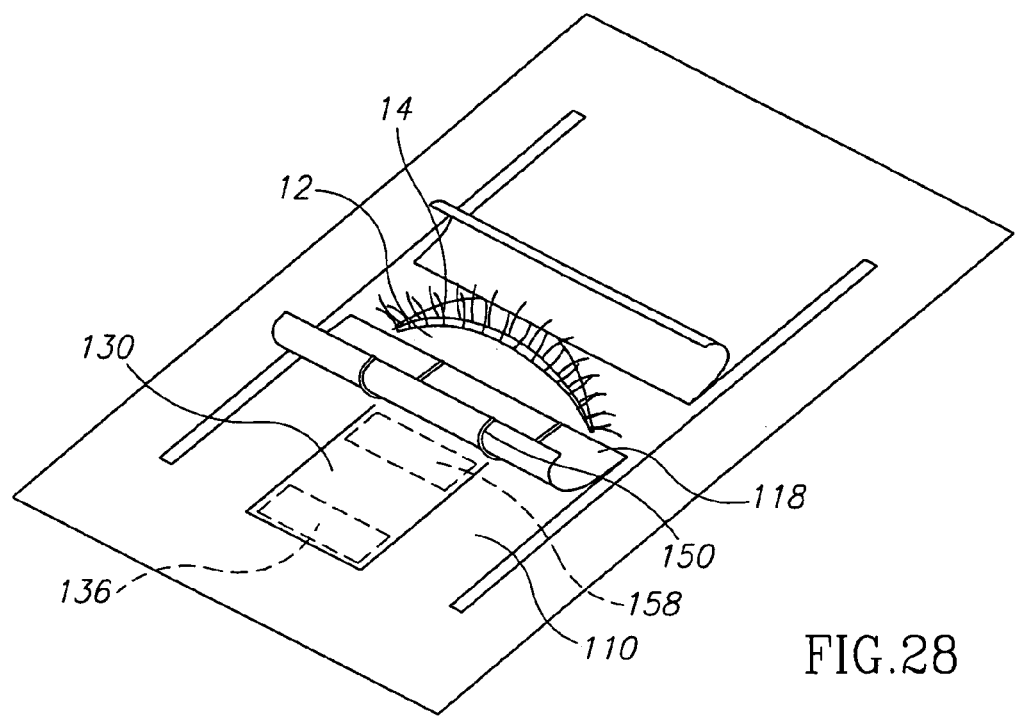
FIG. 28 is an illustration of a drape in accordance with the invention that incorporated the use of multiple self-adherent areas.

The embodiment shown in FIGS. 28 incorporates the use of a self-adherent area 158 that lies underneath the retraction member 110. During the application of the drape system, a surgeon applies pressure to the self-adherent area 158, adhering the retraction member 110 to the facial area 28 on or above the eyelid 12. The surgeon then pulls on retraction flap 130 to partially retract the eyelid 12 away from the eye 10. The non-adherent extension 118 and hooks 150 are then unfolded toward the eye, and are of sufficient length such that the surgeon can then wrap them around the partially retracted eyelid 12. The surgeon then pulls the retraction flap 130 in a direction more tangential to the plane of the retracting member 110 in order to peel the self-adherent area 158 off of facial area 28. This relaxes the forces on the self-adherent area 158 and allows the hooks 150, the non-adherent extension 118 and the eyelid 12 and eyelashes 14 to easily retract and be maintained in the retracted position. The adherent portion 136 on the underside of the retraction flap 130 is applied to the non-adhesive surface 104 of the drape 100 (not shown) to secure the retraction flap 130, hooks 150, the non-adherent extension 118, and the eyelid 12 and eyelashes 14 in a retracted position. This process may be repeated for the corresponding lower elements of the drape system.

Figure 29:
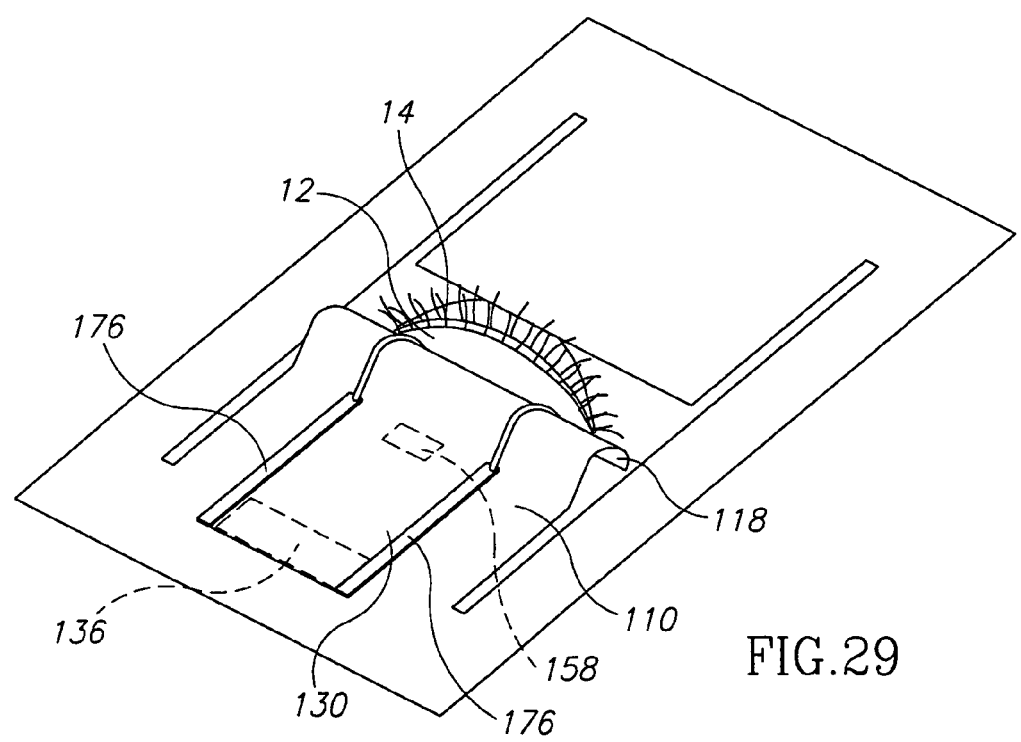
FIG. 29 is an illustration of a drape system in accordance with the invention that incorporates the use of a self-adherent area underneath a retraction member along with reinforcing strips that connect hooks to a strip extension having an adherent portion.
Figure 30:
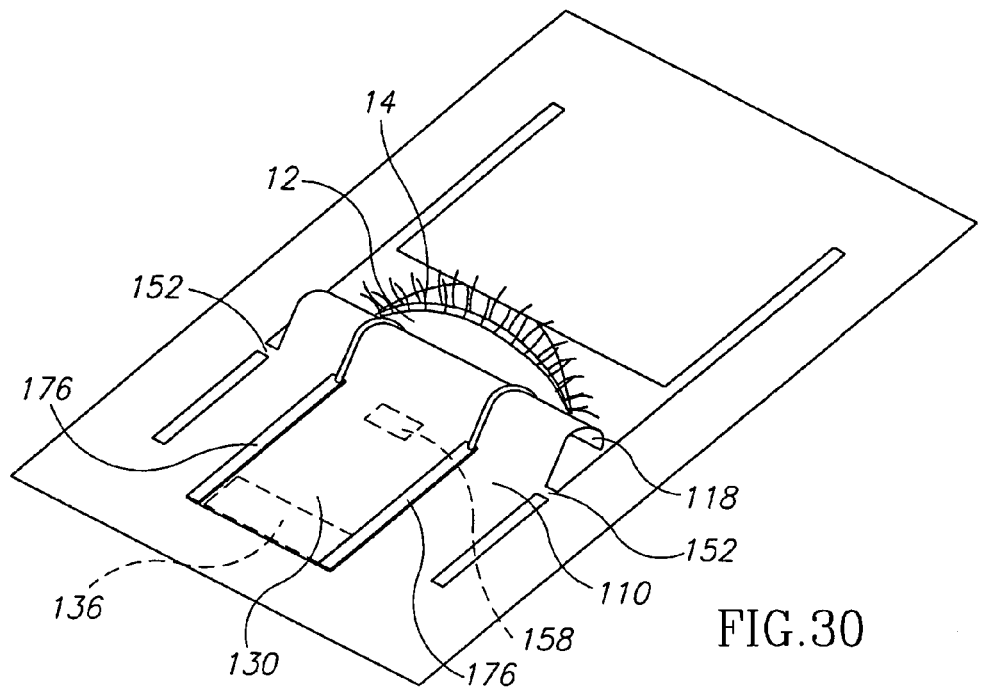
FIG. 30 is an illustration of the drape system shown in FIG. 29, further including bridging elements.

The embodiments shown in FIGS. 29 and 30 incorporate the use of a self-adherent area 158 that lies underneath the retraction member 110 along with reinforcing, nonelastic strips 176 that connect the hooks 150 to retracting flap 130 which has inherent elasticity. During the application of the drape system, a surgeon applies pressure to the self-adherent area 158, adhering the retraction member 110 to the facial area 28 on or above the eyelid 12. The surgeon then pulls on retraction flap 130 to partially retract the eyelid 12 away from the eye 10. The non-adherent extension 118 and hooks 150 are then unfolded toward the eye and the surgeon wraps them around the partially retracted eyelid 12. As the surgeon continues to pull on the retraction flap 130, the elasticity of retracting flap 130 and the inelasticity of strips 176 allow for relative movement between hooks 150 and the self-adherent area 158, thus relaxing the forces on the self-adherent area 158 and allowing the hooks 150, the non-adherent extension 118 and the eyelid 12 and eyelashes 14 to easily retract and be maintained in the retracted position. The adherent portion 136 on the underside of the retraction flap 130 is applied to the non-adhesive surface 104 of the drape 100 (not shown) to secure the retraction flap 118. This process may be repeated for the corresponding lower elements of the drape system.

FIG. 30 illustrates the same drape system described with reference to FIG. 29, further incorporating the use of a bridging element to maintain the retraction member 110 in position within the retraction area 106 until retraction of the eyelids occurs.

Figure 31:
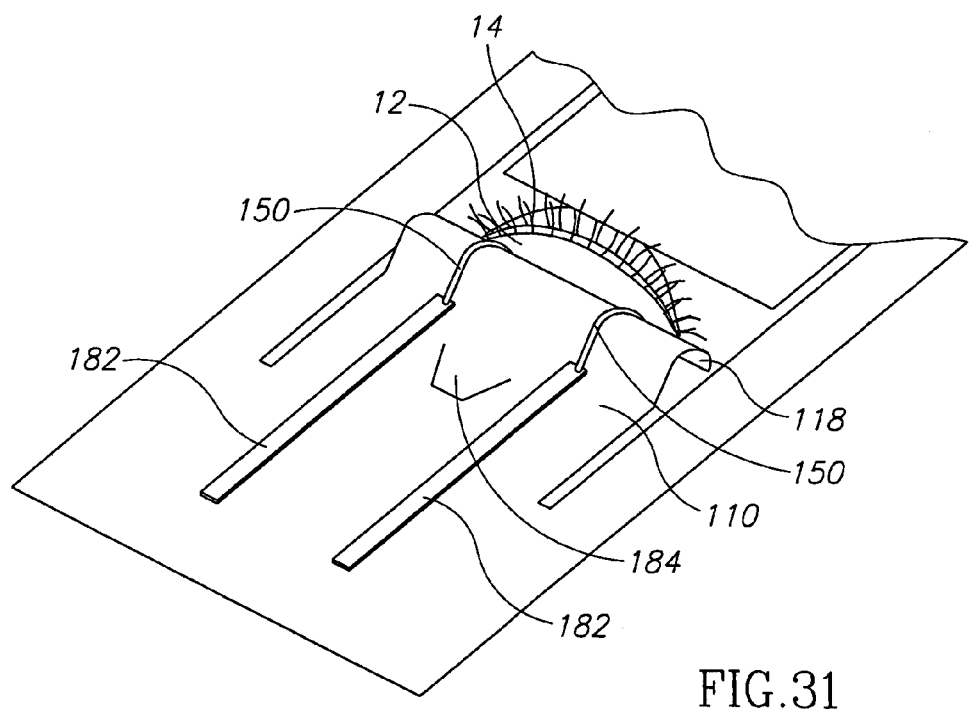
FIG. 31 is an illustration of a drape system in accordance with the invention that incorporates elastic strips or rubber bands.

FIG. 31 illustrates an alternative embodiment of the drape system that eliminates the need for a self-adhering retraction flap through the use of integrated elastic strips or rubber bands 182. During the application of the drape system, a surgeon inserts a finger or tool (not shown) under an access flap 184 and retracts the eyelid 12 away from the eye 10. The rubber bands 182 are stretched in order engage the hooks 150 and non-adherent extension 118 around the eyelid 12. Once engaged, the hooks 150 are released, and the elasticity of the rubber bands 182 retracts and maintains the hooks 150, the non-adherent extension 118 and the eyelid 12 and eyelashes 14 in a retracted position. This process may be repeated for the corresponding lower elements of the drape system.

FIGS. 32 and 33 illustrate yet another embodiment of the drape system of the present invention. This embodiment takes advantage of the natural elasticity of the drape material to obviate the need of any a retraction area 106 defined by slits. A single continuous drape 100 is folded into segments along folds 190 and 192. Hooks 150 and non-adherent extensions 118,120 define the retraction gap 124 between edges 126,128 of the non-adhesive extensions 118,120. An adherent strip 194 is positioned on the undersurface of fold 190 corresponding to a portion of the drape 100 on the front surface of the fold 190 defined at strip 196. In an alternative embodiment, adherent strip 194 is made out of Velcro, and strip 196 is a matching strip of Velcro material. With reference to FIG. 33, the underside of drape 100 includes a self-adherent area 198.

During application of the drape system, a surgeon applies pressure under the fold 190 along the drape 100 at the self-adherent area 198 and retracts the eyelid 12. When the eyelid 12 is sufficiently retracted, the surgeon engages the hooks 150 and non-adherent extension 118 around the eyelid 12 and eyelashes 14. The fold 190 is then pulled away from the eye causing the hooks 150, the non-adherent extension 118 and the eyelid 12 and eyelashes 14 to retract. In a preferred embodiment, Velcro strips 194 and 196 are attached to secure the hooks 150, the non-adherent extension 118 and the eyelid 12 and eyelashes 14 in a retracted position. This process may be repeated for the corresponding lower elements of the drape system.

Figure 34:
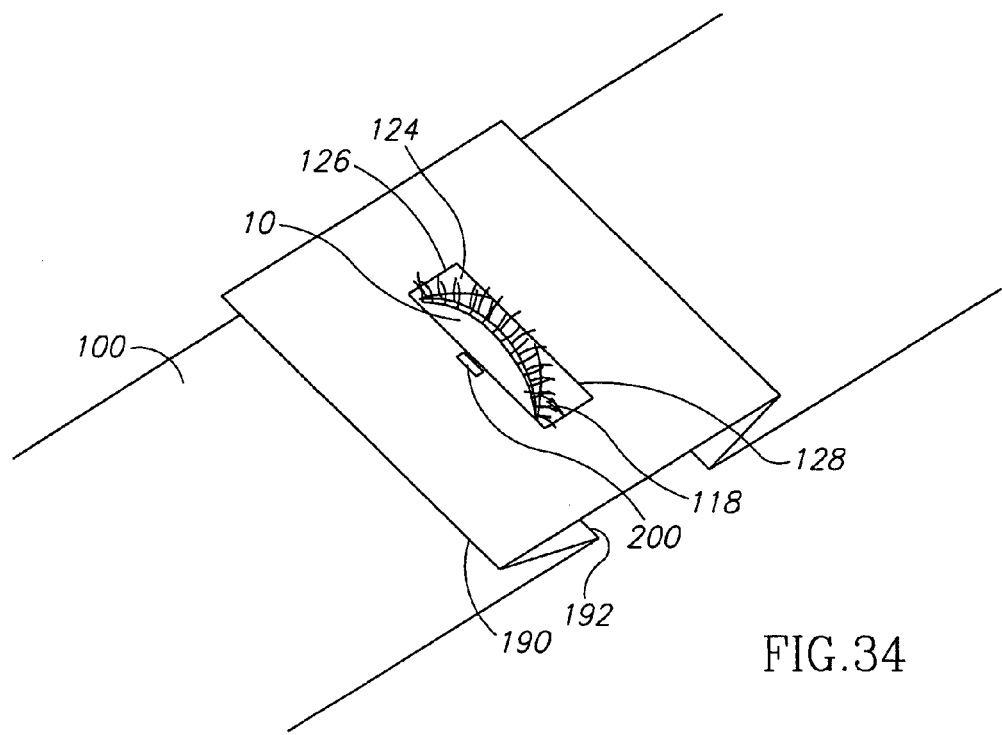
FIG. 34 is an illustration of a drape system in accordance with the invention that incorporates an integrated weight.

FIG. 34 illustrates another embodiment of the drape system of the present invention. This embodiment is for use with an eyelid speculum, but allows a surgeon to use one hand to retract the eyelid while freeing the other hand to wrap the drape around the eyelid and insert the speculum. This obviates the need for having to first secure the eyelid in a retracted position.

The embodiment shown in FIG. 34 is similar to the embodiment described with reference to FIG. 32 except that is does not use hooks or adherent strips 194,196. Instead, this embodiment uses a weight 198 located near the edge 126 of the non-adherent extension 118. As the surgeon retracts the eyelid 12, the weight 198 on indents the drape 100 near the edge 126, allowing the surgeon to easily insert the speculum with one hand while maintaining the eyelid 12 in a retracted state by the continued application of pressure under the fold 190 along the drape 100.

Figure 35:
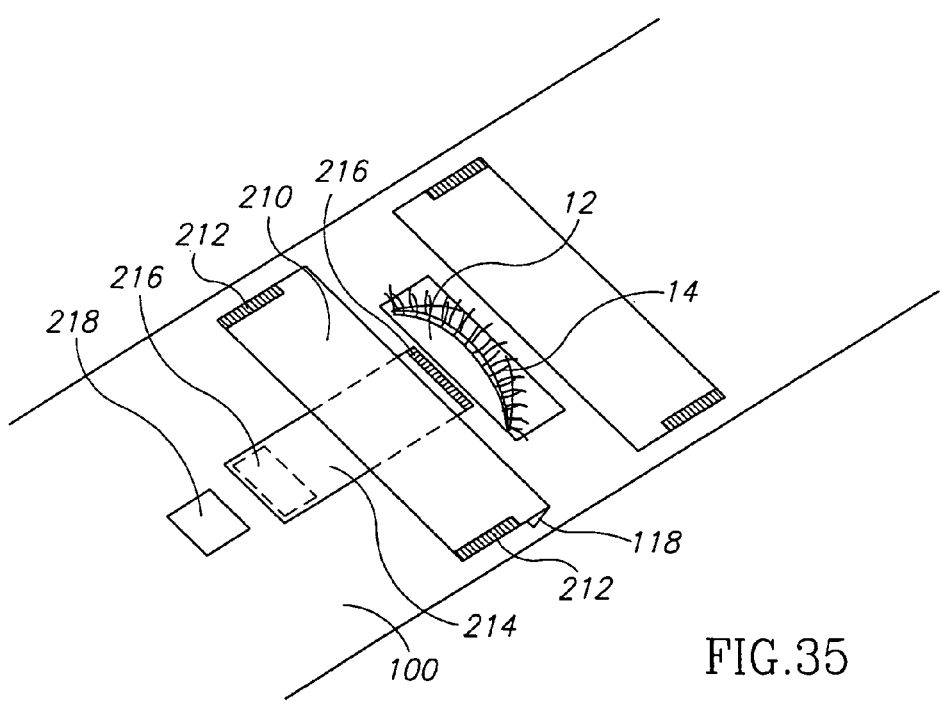
FIG. 35 is an illustration of a drape system in accordance with the invention that incorporates the use of a non-adherent extension located on a second layer rather than attached to a retracting member.

FIG. 35 illustrates another embodiment in which the non-adherent extension 118 is located on a second layer 210 rather than attached to a retracting member. This second layer 210 is attached to the drape 100 at areas 212. A separate retracting strap 214 is attached to the drape 100 at 216, and lies underneath the second layer 210. On the underside and at the opposite end of retracting strap 214 is a Velcro strip 216, and the matching Velcro strip at 218 on drape 100. The undersurface of drape 100 adheres to the skin around the eye. The surgeon pulls the retracting strap 214 away from the eye, which retracts the eyelid underneath the non-adherent extension 118 and second layer 210, where the non-adherent extension is already positioned to drop down around the lid margin, and the Velcro strips 216 and 218 are engaged to maintain the lid in a retracted position so that an external speculum can then be applied. A variation of this embodiment does not include the retraction strap 214. In this alternative embodiment, the surgeon reaches under the second layer 210 and pulls the drape 100 away from the eye directly to retract the eyelid.

Figure 36:
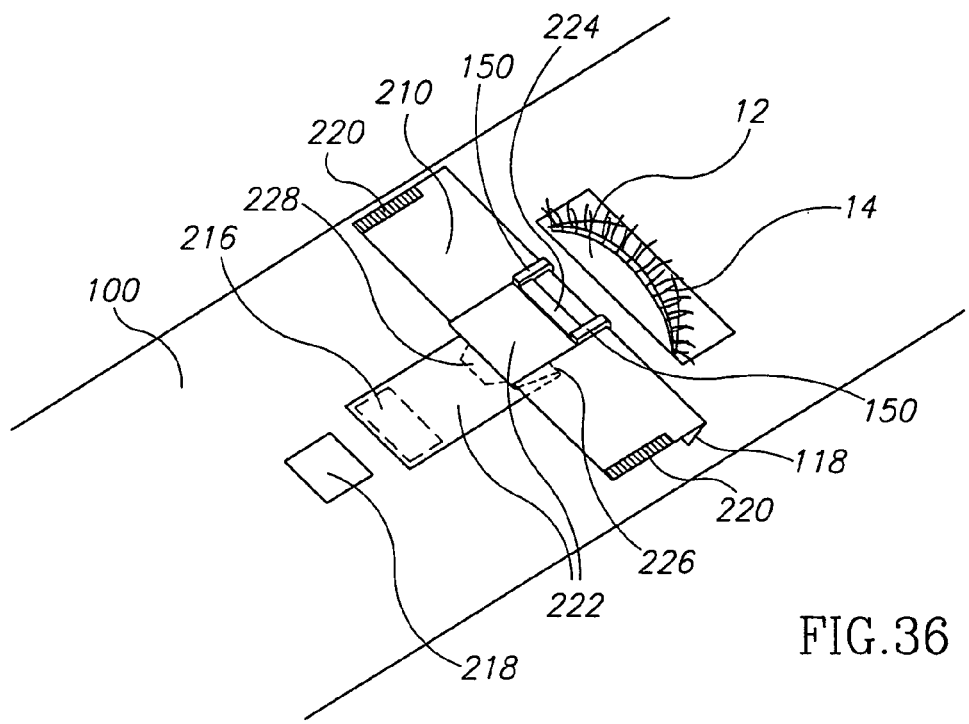
FIGS. 36–38 are illustrations of a drape system in accordance with the invention that incorporates the use of a non-adherent extension located on a second layer rather than attached to a retracting member, further including the use of hooks.
Figure 37:
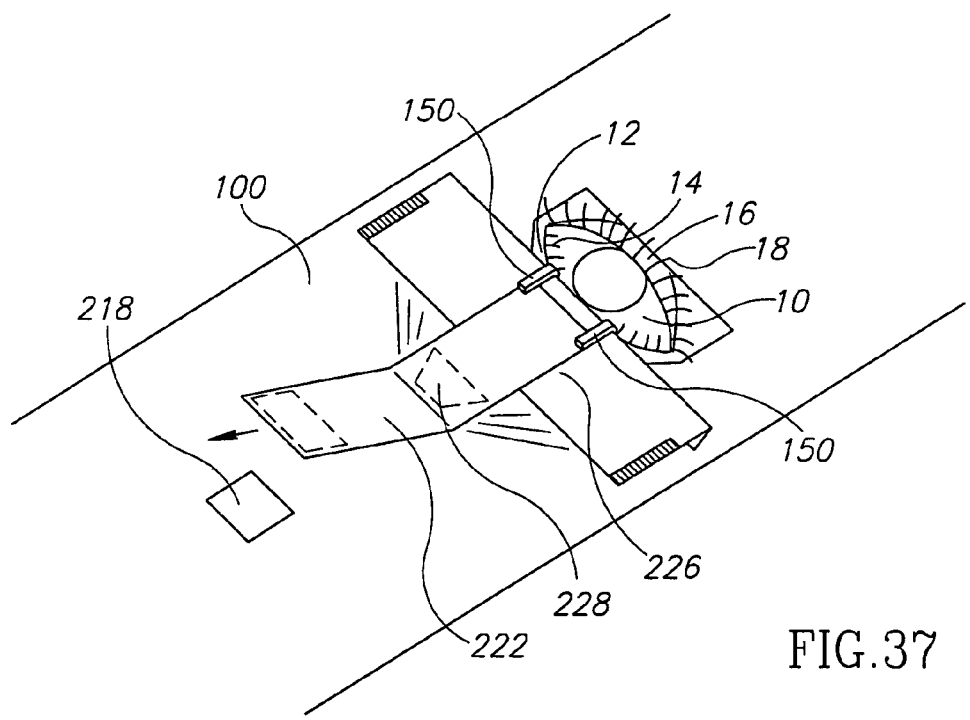
Figure 38:
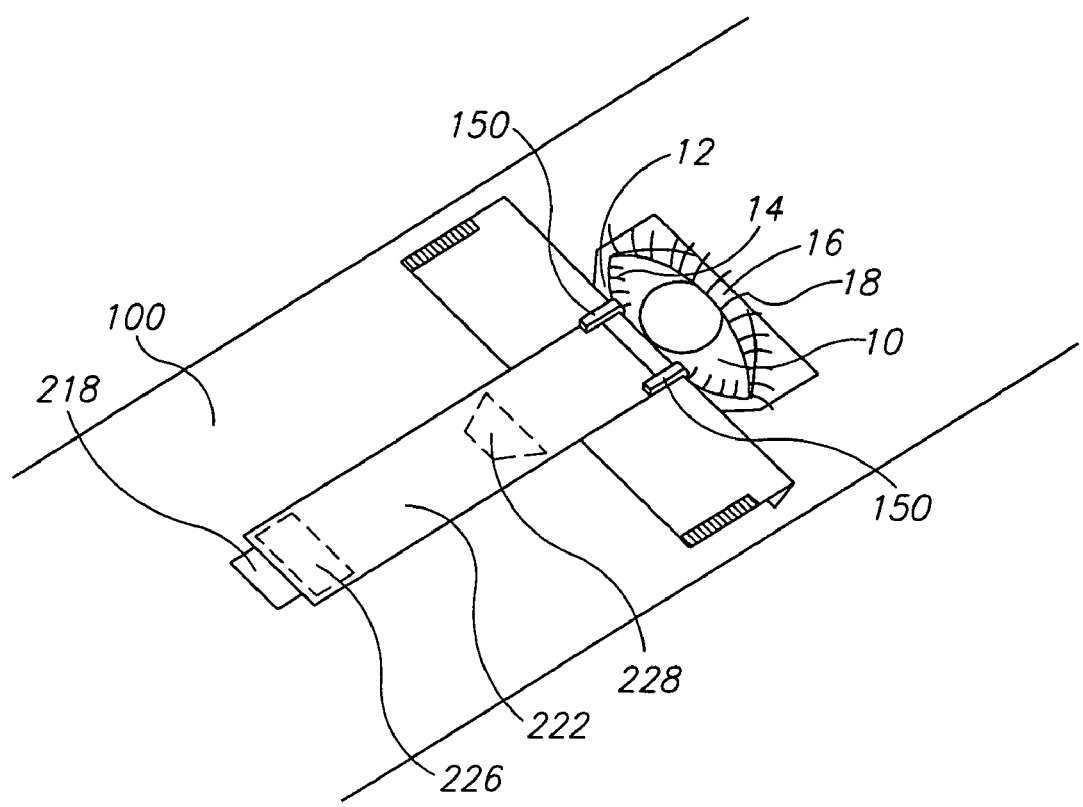

FIGS. 36–38 illustrate an embodiment similar to FIG. 35 further including the use of hooks. A second layer 210 has a non-adherent extension 118, and is attached to drape 100 at areas 220. A retracting strap 222 is attached to the second layer 210 and hooks 150 at area 224. This retracting strap 222 is folded underneath the second layer 210 at 226. At the opposite end and underneath the retracting strap 222 are a Velcro strip 216 and the corresponding Velcro strip 218 on the drape 100. There is s self-adherent area 228 underneath the retracting strap 222, which binds the retracting strap 222 to the surface of drape 100. The surgeon grasps the end of the retracting strap 222 near the Velcro 216 and pulls it away from the eye, which retracts the self-adherent area 228, and consequently the drape surface and eyelid, such that the eyelid lies underneath the non-adherent extension 118, hooks 150, and second layer 210, as shown in FIG. 37.

Referring again to FIG. 37, the surgeon continues traction on strap 222, while the hooks 150 and non-adherent extension 118 are positioned around the lid margin. Then the surgeon pulls the retracting strap 222 in a more tangential direction to the plane of the drape 100 in order to release the self-adherent area 228 from the surface of drape 100. Once the self-adherent area 228 has released, the surgeon then attaches the Velcro strip 216 to the corresponding Velcro strip 218 to secure the hooks 150, non-adherent extension 118 and eyelid in a retracted position, as shown in FIG. 38. In this embodiment, the fold 226 allows for relative movement to engage the lid margin, and the release of self-adherent area 228 allows for relative movement when further retracting and securing the eyelid. Other embodiments might include a variety of mechanisms to allow for the relative movement of the drape elements and to provide for the release of area 228, such as a snap or sliding snap mechanism or other latching mechanism.

While the preferred embodiment of the invention has been illustrated and described, as noted above, many changes can be made without departing from the spirit and scope of the invention. In many described embodiments the precise order in which the drape, drape elements or speculum is applied may be varied while realizing the advantages of the present invention. Accordingly, the scope of the invention is not limited by the disclosure of the preferred embodiment. Instead, the invention should be determined entirely by reference to the claims that follow.

The embodiments of invention in which an exclusive property or privilege is claimed are defined as follows:

1. A drape assembly for use around a patient's eye to seclude and seal off the operative field during eye surgery, comprising:
    a drape having a non-adherent side and an adherent side, the adherent side amenable to adherence to the patient's facial area around the patient's eye;
    an extension member connected to the drape and configured to substantially enclose the patient's eyelid; and
    a retraction flap connected to the drape, wherein the retraction flap is configured to secure the patient's eyelid in a substantially retracted position.

2. The drape assembly of claim 1, further comprising a retraction member connected to the drape and configured to engage the patient's eyelid.

3. The drape assembly of claim 2, wherein the retraction member comprises a first side and a second side, the second side having an adherent section configured to engage the patient's face to enable retraction of the patient's eyelid.

4. The drape assembly of claim 2, wherein:
    the extension member is connected to the retraction member in part by a substantially rigid but malleable material; and
    the substantially rigid but malleable material is configured to fold the extension member so as to substantially enclose the patient's eyelid.

5. The drape assembly of claim 4, wherein the substantially rigid material is in the shape of a hook.

6. The drape assembly of claim 2, further comprising:
    at least one substantially rigid fastener attached to the retraction member; and
    wherein the at least one substantially rigid fastener is configured to engage the patient's eyelid.

7. The drape assembly of claim 6, wherein the substantially rigid fastener is a hook.

8. The drape assembly of claim 6, wherein the substantially rigid fastener is a rotatable rod.

9. The drape assembly of claim 2, further comprising:
a least one elastic strip connecting the at least one substantially rigid fastener to the retraction member; and
wherein at least one elastic strip is configured to retract the at least one substantially rigid fastener to secure the patient's eyelid in a substantially retracted position.

10. The drape assembly of claim 2, further comprising a second retraction member positioned between the first retraction member and the patient's eyelid, the second retraction member configured to engage the patient's eyelid.

11. The drape assembly of claim 2, further comprising at least one bridging element connecting the retraction member to the drape.

12. The drape assembly of claim 1, wherein the extension member is formed of a substantially rigid material.

13. The drape assembly of claim 1, wherein the retraction flap comprises a first side and a second side, the second side having an adherent section configured to engage the drape to secure the patient's eyelid in a substantially retracted position.

14. A drape assembly for use around a patient's eye to seclude and seal off the operative field during eye surgery, comprising:
a drape having a non-adherent side and an adherent side, the adherent side comprising an adhesive adapted to directly adhere to a substantial area of a patient's skin surrounding the patient's eye;
a retraction member connected to the drape and adapted to secure directly to the patient's eyelid; and
an extension member connected to the drape proximate the retraction member and having a portion selectively positionable to substantially enclose the patient's eyelid when the retraction member is secured to the patient's eyelid.

15. The drape assembly of claim 14, wherein the drape defines an opening positionable over the patient's eye, the retraction member being positioned proximate the opening, the extension member securing to the drape proximate the opening and having a portion thereof positionable within the opening when the retraction member is secured to the patient's eyelid.

16. The drape assembly of claim 15, wherein the retraction member comprises an adhesive area proximate the opening in a position to engage the eyelid of the patient having the eye positioned in the opening.

17. The drape of claim 14, wherein the retraction member has a fixed end directly connected to the drape, and an exposed end and wherein the extension member secures to the retraction member proximate the exposed end.

18. The drape of claim 14, wherein the retraction member is monolithically formed with the drape.

19. The drape of claim 14, wherein the extension member is more rigid than the drape.

20. The drape assembly of claim 14, wherein the retraction member is a first retraction member adapted to secure directly to the patient's upper eyelid and the extension member is a first extension member selectively positionable to substantially enclose the patient's upper eyelid when the first retraction member is secured to the patient's upper eyelid.

21. The drape assembly of claim 20, further comprising:
a second retraction member connected to the drape and adapted to secure directly to the patient's lower eyelid; and
a second extension member connected to the drape and having a portion thereof selectively positionable to substantially enclose the patient's lower eyelid when the second retraction member is secured to the patient's lower eyelid.

22. The drape assembly of claim 14, further comprising a second retraction member.

23. A drape assembly for use around a patient's eye to seclude and seal off the operative field during eye surgery, comprising:
a drape having a non-adherent side and an adherent side, the adherent side amenable to adherence to the patient's facial area around the patient's eye;
a retraction member connected to the drape and adapted to secure directly to the patient's eyelid; and
an extension member connected to the drape proximate the retraction member and having a portion selectively positionable to substantially enclose the patient's eyelid when the retraction member is secured to the patient's eyelid;
wherein the drape defines an opening positionable over the patient's eye, the retraction member being positioned proximate the opening, the extension member securing to the drape proximate the opening and having a portion thereof positionable within the opening when the retraction member is secured to the patient's eyelid; and
wherein the extension member comprises a strip formed of thin material secured along a longer dimension of the strip to the drape proximate the opening.

24. The drape assembly of claim 23, wherein the strip has a width greater than or equal that of the opening.

25. A drape assembly for use around a patient's eye to seclude and seal off the operative field during eye surgery, comprising:
a drape having a non-adherent side and an adherent side, the adherent side amenable to adherence to the patient's facial area around the patient's eye;
a frangible portion formed in the drape, the frangible portion being rupturable to create an elongate opening extending thereacross;
a substantially non-frangible portion completely encircling the frangible portion; and
an extension member connected to the drape proximate the frangible portion and configured to substantially enclose the patient's eyelid.

26. The drape of claim 25, wherein the frangible portion comprises a plurality of bridges extending between a plurality of slits formed in the drape.

27. The drape assembly of claim 26, wherein the plurality of bridges has a width substantially less than the length of the elongate opening.

28. The drape assembly of claim 26, wherein the bridge is readily broken.

29. The drape assembly of claim 25, wherein the extension member substantially encloses the eyelid margin.

30. A drape assembly for use around a patient's eye to seclude and seal off the operative field during eye surgery, comprising:
a drape having a non-adherent side and an adherent side, the adherent side amenable to adherence to the patient's facial area around the patient's eye;
a frangible portion formed in the drape, the frangible portion being rupturable to create an elongate opening extending thereacross and comprising a plurality of bridges extending between a plurality of slits formed in the drape;

an extension member connected to the drape proximate the frangible portion and configured to substantially enclose the patient's eyelid; and a retraction member secured to the drape proximate the opening and configured to secure to the patient's eyelid.

31. A drape assembly for use around a patient's eye to seclude and seal off the operative field during eye surgery, comprising:

a drape having a non-adherent side and an adherent side, the adherent side amenable to adherence to a facial area of the patient substantially surrounding the patient's eye;

a retraction member connected to the drape and adapted to secure directly to the patient's eyelid; and an extension member connected to the drape proximate the retraction member and having a portion selectively positionable to substantially enclose the patient's eyelid when the retraction member is secured to the patient's eyelid;

wherein the retraction member is connected to the drape distanced from a perimeter of the drape and having an adhesive underside adapted to adhere directly to an upper surface of the patient's eyelid; and wherein the extension member is connected to the drape distanced from the perimeter of the drape, the extension member having a non-adhesive underside facing the same as the adhesive underside of the retraction member when undeformed, the extension member selectively positionable contacting an inner surface of the patient's eyelid when the retraction member is secured to the patient's eyelid.

* * * * *